(12) United States Patent
Gobbi et al.

(10) Patent No.: US 7,795,437 B2
(45) Date of Patent: Sep. 14, 2010

(54) ETHER DERIVATIVES

(75) Inventors: Luca Claudio Gobbi, Oberwil BL (CH);
Georg Jaeschke, Basel (CH); Olivier Roche, Folgensbourg (FR); Rosa Maria Rodriguez Sarmiento, Basel (CH);
Lucinda Steward, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 170 days.

(21) Appl. No.: 11/876,007

(22) Filed: Oct. 22, 2007

(65) Prior Publication Data

US 2008/0103174 A1    May 1, 2008

(30) Foreign Application Priority Data

Oct. 31, 2006  (EP)  .................. 06123274

(51) Int. Cl.
*C07D 215/12*  (2006.01)
*C07D 401/00*  (2006.01)
(52) U.S. Cl. ....................... 546/168; 546/201
(58) Field of Classification Search ................ 546/168, 546/201
See application file for complete search history.

(56) References Cited

FOREIGN PATENT DOCUMENTS

| DE | 2536103 | 2/1976 |
|---|---|---|
| EP | 0 479 601 | 4/1992 |
| EP | 1 348 434 | 10/2003 |
| JP | 03 264579 | 11/1991 |
| WO | WO 00/58305 | 10/2000 |
| WO | WO 03/028725 | 4/2003 |
| WO | WO 03/029233 * | 4/2003 |
| WO | WO 03/029233 A1 | 4/2003 |
| WO | WO 03/048154 | 6/2003 |
| WO | WO 2004/063181 | 7/2004 |
| WO | WO 2005/012266 A1 | 2/2005 |

OTHER PUBLICATIONS

Joyce et al., Drug Discovery Today, vol. 10, No. 13 pp. 917-925 (2005).
De Angelis, Curr. Opin. Investig. Drugs vol. 3, pp. 106-112 (2002).
Reavill et al., J. Pharmacol. Exp. Ther. vol. 294 pp. 1154-1165 (2000).
Vorel et al., J. Neurosci. vol. 22, pp. 9595-9603 (2002).
Campos et al., Soc. Neurosci. Online Abstract 322.8 (2003).
Ashby et al., Synapse, vol. 48, pp. 154-156 (2003).
Drescher. et al., Am. Soc. Neurosci. Online Abstract 894.6 (2002).
Roth et al., Nat. Rev. Drug Discov. vol. 3, pp. 353-359 (2004).
Lieberman, et al., N. Engl. J. Med. vol. 353, pp. 1209-1223 (2005).
Missale, et al., Physiol. Rev. vol. 78, pp. 189-225 (1998).
Gurevic et al., Neuropsychopharmacology, vol. 20, pp. 60-80 (1998).
Gurevic et al., Arch. Gen. Psychiatry, vol. 54, pp. 225-232 (1997).
Leikin J. et al., Med. Toxicol. Adverse Drug Exp. vol. 4, pp. 324-350 (1989).
Harrison, P. J., Br. J. Psychiatry Suppl. 174, vol. 38, pp. 12-22 (1999).
Barnes, et al., Neuropharmacology, vol. 38, pp. 1083-1152 (1999).
Pompeiano et al., Molecular Brain Research vol. 23, pp. 163-178 (1994).
Pazos et al., Neuroscience vol. 21, pp. 123-139 (1987).
Roth et al., Pharmacol. Ther. vol. 79 pp. 231-257 (1998).
Spurlock et al., Mol. Psychiatry, vol. 3 pp. 42-49 (1998).
Arranz et al., Lancet vol. 355, pp. 1615-1616 (2000).
Porras et al., Neuropsychopharmacology, vol. 26, pp. 311-324 (2002).
Meltzer et al., J. Pharmacol. Exp. Ther. vol. 251, pp. 238-246 (1989).
Wustrow et al., Journal of Medicinal Chem. vol. 41, pp. 760-771 (1998).
Tokuyama et al., Synthesis, vol. 8, pp. 1121-1123 (2002).
Bernacka et al., Tetrahedron Letters, vol. 42 pp. 5093-5094 (2001).
Mancuso, A. et al., Synthesis, pp. 165-185 (1981).
Herndon, J.L., et al., Journal of Medicinal Chemistry, vol. 35, pp. 4903-4910 (1992), XP000941731.
Watanabe, Y., et al., Chemical and Pharmaceutical Bulletin, vol. 38, No. 10, pp. 2726-2732 (1990), XP001018922.
Belliotti, T.R., et al., Bioorganic & Medicinal Chemistry Letters, vol. 7, No. 18, pp. 2403-2408 (1997), XP002378782.

* cited by examiner

*Primary Examiner*—D. Margaret Seaman
*Assistant Examiner*—Nizal S Chandrakumar
(74) *Attorney, Agent, or Firm*—George W. Johnston; Patricia S. Rocha-Tramaloni; Kimberly J. Prior

(57) ABSTRACT

The present invention relates to ether derivatives according to general formula I,

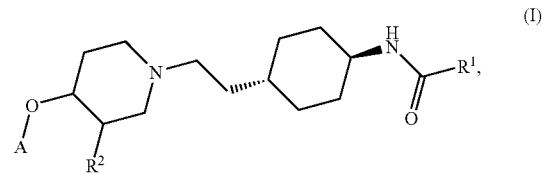

and to their pharmaceutically-acceptable salts, which may be used in treating or preventing cognitive disorders, drug addiction, depression, anxiety, drug dependence, dementias, memory impairment, psychotic disorders comprising schizophrenia, schizoaffective disorders, bipolar disease, mania, psychotic depression, or psychoses comprising paranoia and delusions.

17 Claims, No Drawings

ETHER DERIVATIVES

PRIORITY TO RELATED APPLICATION(S)

This application claims the benefit of European Patent Application No. 06123274.0, filed Oct. 31, 2006, which is hereby incorporated by reference in its entirety.

FIELD OF THE INVENTION

The present invention relates to ether derivatives which are dual modulators of serotonin 5-HT$_{2A}$ and dopamine D$_3$ receptors.

BACKGROUND OF THE INVENTION

Schizophrenia is characterized by complex symptomatology including positive symptoms, (i.e. delusions and hallucinations), and negative symptoms, (i.e. anhedonia, restricted fluency and productivity of thought and speech). In addition, it is now well recognized that cognitive impairment is the third major diagnostic category of schizophrenia, characterized by loss in working memory as well as other deficits. Other symptoms include aggressiveness, depression and anxiety (Stahl, S. M. (2000) Essential Psychopharmacology. Neuroscientific Basis and Practical Applications. Cambridge University Press, second edition, Cambridge, UK). The different categories and the clinical features of the disorder are defined in diagnostic schemes such as DSM-IV (Diagnostic and statistical manual of mental disorders, 4$^{th}$ edition) or ICD-10 (International classification of diseases, 10$^{th}$ edition). Currently, medication used to treat schizophrenia, bipolar mania and other psychoses include antipsychotics. Such antipsychotics include both typical antipsychotics (D$_2$/D$_3$ preferring) and atypical antipsychotics. Atypical antipsychotics exhibit polypharmacology in that they interact at multiple receptors (e.g., D$_1$, D$_2$, D$_3$, D$_4$, 5-HT$_{1A}$, 5-HT$_{2A}$, 5-HT$_{2C}$, H$_1$, M$_1$, M$_2$, M$_4$ etc; Roth, B. L et al. (2004) Magic shotguns versus magic bullets: selectively non-selective drugs for mood disorders and schizophrenia. Nat. Rev. Drug Discov. 3, 353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems (Lieberman J. A., et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223). Furthermore, patient compliance is compromised by prevalent side effects such as weight gain, extrapyramidal symptoms (EPS), and cardiovascular effects (Lieberman J. A. et al. Clinical Antipsychotic Trials of Intervention Effectiveness (CATIE) Investigators. (2005) Effectiveness of antipsychotic drugs in patients with chronic schizophrenia. N. Engl. J. Med. 353, 1209-1223).

Dopamine, a major catecholamine neurotransmitter, is involved in the regulation of a variety of functions which include emotion, cognition, motor functions, and positive reinforcement, (Purves, D. et al. (2004) Neuroscience. Sinauer, third edition, Sunderland, Mass.). The biological activities of dopamine are mediated through G protein-coupled receptors (GPCRs). In humans, five different dopamine receptors D$_1$-D$_5$ have been identified, where the D$_2$-like receptors (D$_2$, D$_3$ and D$_4$) couple to the G-protein GC, (Missale, C. et al. (1998) Dopamine receptors: from structure to function. Physiol. Rev. 78, 189-225). The D$_3$ dopamine receptor is most highly expressed in the nucleus accumbens (Gurevich, E. V., Joyce, J. N. (1999) Distribution of dopamine D$_3$ receptor expressing neurons in the human forebrain: comparison with D$_2$ receptor expressing neurons. Neuropsychopharmacology 20, 60-80) and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus D$_3$ receptor antagonists are proposed to modulate psychotic symptoms such as hallucinations, delusions and thought disorder (Joyce, J. N. and Millan M. J., (2005) Dopamine D$_3$ receptor antagonists as therapeutic agents. Drug Discovery Today, {Drug-Discov-Today}, 1 July, Vol. 10, No. 13, P. 917-25, Issn: 1359-6446), while these antagonists spare the D$_2$ modulated striatal extrapyramidal system (associated with EPS induction). In addition, it has been reported that drug naive schizophrenic patients show altered levels of D$_3$ receptor expression (Gurevich, E. V. et al. (1997) Mesolimbic dopamine D$_3$ receptors and use of antipsychotics in patients with schizophrenia. A postmortem study. Arch. Gen. Psychiatry 54, 225-232) and dopamine release (Laruelle, M. (2000) Imaging dopamine dysregulation in schizophrenia: implication for treatment. Presented at Workshop Schizophr.: Pathol. Bases and Mech. Antipsychotic Action, Chicago), indicating that a disturbed homeostasis of dopamine plays an important role in the etiology of schizophrenic symptoms.

The neurotransmitter serotonin is implicated in several psychiatric conditions including schizophrenia (Kandel, E. R. et al. (eds.; 2000) Principles of Neural Science, 3$^{rd}$ edition Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin, J. B. et al. (1989) Clinical features and management of intoxication due to hallucinogenic drugs. Med. Toxicol. Adverse Drug Exp. 4, 324-350). Furthermore, altered brain distribution of serotonin receptors as well as an altered serotonergic tone, have been detected in schizophrenic patients (Harrison, P. J. (1999) Neurochemical alterations in schizophrenia affecting the putative receptor targets of atypical antipsychotics. Focus on dopamine (D$_1$, D$_3$, D$_4$) and 5-HT$_{2A}$ receptors. Br. J. Psychiatry Suppl. 38, 12-22). In mammals serotonin exerts its biological activities through a family of 14 5-HT GPCRs (Barnes, N. M., Sharp, T. (1999) A review of central 5-HT receptors and their function. Neuropharmacology 38, 1083-1152). The 5-HT$_{2A}$ receptor is most prominently expressed in the prefrontal cortex and at lower levels in the basal ganglia and the hippocampus in human brain (Pompeiano, M. et al. (1994) Distribution of the serotonin 5-HT2 receptor family mRNAs: comparison between 5-HT$_{2A}$ and 5-HT$_{2C}$ receptors. Brain Res. Mol. Brain. Res. 23, 163-178; Pazos, A., Probst, A., Palacios, J. M. (1987) Serotonin receptors in the human brain-IV. Autoradiographic mapping of serotonin-2 receptors. Neuroscience 21, 123-139), and is coupled predominantly to the G-protein Guq (Roth, B. L. et al. (1998) 5-Hydroxytryptamine-2-family receptors (5-hydroxytryptamine2A, 5-hydroxytryptamine2B, 5-hydroxytryptamine2C): where structure meets function. Pharmacol. Ther. 79, 231-257). Genetic linkage studies of a 5-HT$_{2A}$ polymorphism to schizophrenia (Spurlock, G. et al. (1998) A family based association study of T102C polymorphism in 5HT$_{2A}$ and schizophrenia plus identification of new polymorphisms in the promoter.

Mol. Psychiatry. 3, 42-49), as well as responsiveness to antipsychotic drugs (Arranz, M. J. et al. (2000) Pharmacogenetic prediction of clozapine response. Lancet 355, 1615-1616), further suggests a role for the 5-$HT_{2A}$ receptor both in the treatment and pathology of psychosis. In addition, dopaminergic neurotransmission appears to be under the afferent regulation of the 5-$HT_{2A}$ receptor (Porras, G. et al. 5-$HT_{2A}$ and 5-$HT_{2C/2B}$ receptor subtypes modulate dopamine release induced in vivo by amphetamine and morphine in both the rat nucleus accumbens and striatum. Neuropsychopharmacology 26, 311-324-2002). Overall 5-$HT_{2A}$ receptor antagonists are proposed to be suitable for the treatment of disorders associated with dysfunctional dopaminergic systems. Moreover, 5-$HT_{2A}$ receptor antagonism has been recognized as beneficial for the treatment of psychosis (reviewed in de Angelis, L. (2002) 5-$HT_{2A}$ antagonists in psychiatric disorders. Curr. Opin. Investig. Drugs 3, 106-112) and indeed is one of the defining features of so-called atypical antipsychotic drugs which are characterized by a relatively high affinity for the 5-$HT_{2A}$-relative to the $D_2$ receptor (Meltzer, H. Y. et al. (1989) Classification of typical and atypical antipsychotic drugs on the basis of dopamine D-1, D-2 and serotonin2 pKi values. J. Pharmacol. Exp. Ther. 251, 238-246).

We found that the compounds of the present invention are dual modulators of the serotonin 5-$HT_{2a}$ and dopamine $D_3$ receptors.

The compounds of the invention have high affinity for the dopamine $D_3$ and serotonin (5-Hydroxytryptamine; 5-HT) 5-$HT_{2A}$ receptors and are believed to be effective in the treatment of psychotic disorders, as well as other diseases such as depression and anxiety, drug dependence, dementias and memory impairment. Psychotic disorders encompass a variety of diseases, which include schizophrenia, schizoaffective disorders, bipolar disease, mania, psychotic depression, and other psychoses involving paranoia and delusions (Reavill-C –et al. (2000) Pharmacological actions of a novel, high-affinity, and selective human dopamine $D_3$ receptor antagonist, SB-277011-A. JPET 294:1154-1165; Harrison, P. J. (1999) Neurochemical alterations in schizophrenia affecting the putative receptor targets of atypical antipsychotics. Focus on dopamine ($D_1$, $D_3$, $D_4$) and 5-$HT_{2A}$ receptors. Br. J. Psychiatry Suppl. 38, 12-22; de Angelis, L. (2002) 5-$HT_{2A}$ antagonists in psychiatric disorders. Curr. Opin. Investig. Drugs 3, 106-112; Joyce, J. N. and Millan M. J., (2005) Dopamine $D_3$ receptor antagonists as therapeutic agents. Drug Discovery Today, {Drug-Discov-Today}, 1 July, Vol. 10, No. 13, P. 917-25, Issn: 1359-6446); drug dependency and abuse and withdrawal (Vorel, S. R. et al. E. L (2002) Dopamine $D_3$ receptor antagonism inhibits cocaine-seeking and cocaine-enhanced brain reward in rats. J. Neurosci., 22, 9595-9603; Campos, A. C. et al. (2003) The dopamine $D_3$ receptor antagonist SB277011A antagonizes nicotine-enhanced brain-stimulation reward in rat. Soc. Neurosci. Abstr., 322.8; Ashby, C. R., et al. (2003). Acute administration of the selective $D_3$ receptor antagonist SB-277011-A blocks the acquisition and expression of the conditioned place preference response to heroin in male rats. Synapse, 48, 154-156); anxiety, and depression (Reavill-C et al. (2000) Pharmacological actions of a novel, high-affinity, and selective human dopamine $D_3$ receptor antagonist, SB-277011-A. JPET 294:1154-1165; Drescher, K. et al. (2002) In vivo effects of the selective dopamine $D_3$ receptor antagonist A-437203. Am. Soc. Neurosci. 894.6). As such, the compounds of the present invention are proposed to treat psychoses and other diseases, with fewer associated side affects than those exhibited by prior art compounds.

SUMMARY OF THE INVENTION

The present invention relates to a compound according to general formula I:

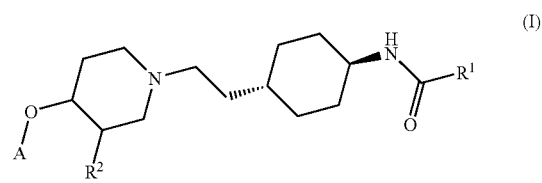

wherein:

A is selected from the group consisting of: aryl and 5- to 12-membered heteroaryl, wherein said aryl or heteroaryl is optionally substituted by at least one substituent, each said substituent independently selected from the group consisting of:
  halogen,
  cyano,
  $C_{1-6}$-alkyl optionally substituted by cyano or $C_{1-6}$-alkoxy,
  $C_{1-6}$-alkoxy, and
  —$S(O)_2$—$C_{1-6}$-alkyl;

$R^1$ is selected from the group consisting of:
  $C_{1-6}$-alkyl optionally substituted by at least one substituent, each of said substituent being independently selected from the group consisting of: halogen, $C_{1-6}$-alkoxy, and aryl optionally substituted by halogen;
  $C_{3-10}$-cycloalkyl optionally substituted by one or more $R^a$;
  5- to 12-membered heterocycloalkyl optionally substituted by one or more $R^a$;
  aryl optionally substituted by one or more $R^a$;
  5- to 12-membered heteroaryl optionally substituted by one or more $R^a$; and
  —$NR^bR^c$, wherein $R^b$ is hydrogen or $C_{1-6}$-alkyl and $R^c$ is hydrogen,
  $C_{1-6}$-alkyl or aryl optionally substituted by one or more $R^a$;

each $R^a$ is independently selected from the group consisting of:
  halogen;
  —$S(O)_2$—$C_{1-6}$-alkyl;
  cyano;
  oxo;
  $C_{1-6}$-alkyl optionally substituted by aryl which is substituted by halogen;
  $C_{1-6}$-haloalkyl;
  $C_{1-6}$-haloalkoxy;
  $C_{1-6}$-alkoxy optionally substituted by 5- to 6-membered heteroaryl which is optionally substituted by $C_{1-6}$-alkyl;
  —NH(CO)—$C_{1-6}$-alkyl;
  5- to 6-membered heterocycloalkyl; and
  5- to 6-membered heteroaryl optionally substituted by $C_{1-6}$-alkyl or oxo; and $R^2$ is selected from the group consisting of hydrogen and hydroxyl;

and to a pharmaceutically-acceptable salt of such a compound.

The invention relates also to a pharmaceutical composition comprising a compound of the aforementioned formula or a pharmaceutically-acceptable salt thereof.

Another aspect of the present invention is a process for the preparation of a compound of the aforementioned formula

DETAILED DESCRIPTION OF THE INVENTION

The present invention relates to a compound according to general formula I:

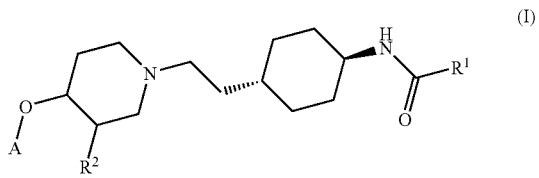

wherein:

A is selected from the group consisting of: aryl and 5- to 12-membered heteroaryl, wherein said aryl or heteroaryl is optionally substituted by at least one substituent, each said substituent independently selected from the group consisting of:
  halogen,
  cyano,
  $C_{1-6}$-alkyl optionally substituted by cyano or $C_{1-6}$-alkoxy,
  $C_{1-6}$-alkoxy, and
  —$S(O)_2$—$C_{1-6}$-alkyl;

$R^1$ is selected from the group consisting of:
  $C_{1-6}$-alkyl optionally substituted by at least one substituent, each of said substituent being independently selected from the group consisting of: halogen, $C_{1-6}$-alkoxy, and aryl optionally substituted by halogen;
  $C_{3-10}$-cycloalkyl optionally substituted by one or more $R^a$;
  5- to 12-membered heterocycloalkyl optionally substituted by one or more $R^a$;
  aryl optionally substituted by one or more $R^a$;
  5- to 12-membered heteroaryl optionally substituted by one or more $R^a$; and —$NR^bR^c$, wherein $R^b$ is hydrogen or $C_{1-6}$-alkyl and $R^c$ is hydrogen, $C_{1-6}$-alkyl or aryl optionally substituted by one or more $R^a$;

each $R^a$ is independently selected from the group consisting of:
  halogen;
  —$S(O)_2$—$C_{1-6}$-alkyl;
  cyano;
  oxo;
  $C_{1-6}$-alkyl optionally substituted by aryl which is substituted by halogen;
  $C_{1-6}$-haloalkyl;
  $C_{1-6}$-haloalkoxy;
  $C_{1-6}$-alkoxy optionally substituted by 5- to 6-membered heteroaryl which is optionally substituted by $C_{1-6}$-alkyl;
  —NH(CO)—$C_{1-6}$-alkyl;
  5- to 6-membered heterocycloalkyl; and
  5- to 6-membered heteroaryl optionally substituted by $C_{1-6}$-alkyl or oxo; and $R^2$ is selected from the group consisting of hydrogen and hydroxyl;

and to a pharmaceutically-acceptable salt of such a compound.

Compounds of formula (I) may form acid addition salts with acids, such as conventional pharmaceutically-acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluent). The invention embraces all of these forms.

It will be appreciated, that the compounds of general formula (I) in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

"Aryl" means a monovalent cyclic aromatic moiety consisting of a mono-, bi- or tricyclic aromatic ring wherein each member of the ring is carbon. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, and diphenyl-isopropylidenyl, as well as those specifically illustrated by the examples herein below. Preferred aryl moieties are phenyl and naphthyl with phenyl being more particularly preferred.

The aryl moieties of the invention further can be substituted by one, two or three substituents such as those substituents specifically illustrated in the examples herein below.

"$C_{1-6}$-alkyl" denotes a straight- or branched-carbon chain group containing from 1 to 6 carbon atoms, for example, methyl, ethyl, propyl, isopropyl, isobutyl, sec-butyl, tert-butyl, pentyl, n-hexyl as well as those specifically illustrated by the examples herein below.

"$C_{1-6}$-haloalkyl" denotes a $C_{1-6}$-alkyl group as defined above which is substituted by one or more halogen(s). Examples of $C_{1-6}$-haloalkyl include but are not limited to methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_1$-$C_7$-haloalkyl groups are difluoro- or trifluoro-methyl or ethyl.

"$C_{1-6}$-alkoxy" denotes a group wherein the alkyl group is as defined above and the alkyl group is connected to the remainder of the molecule via an oxygen atom.

"$C_{1-6}$-haloalkoxy" denotes a $C_{1-6}$-alkoxy group as defined above which is substituted by one or more halogen. Examples of $C_{1-6}$-haloalkoxy include but are not limited to methoxy or ethoxy, substituted by one or more Cl, F, Br or I atom(s) as well as those groups specifically illustrated by the examples herein below. Preferred $C_1$-$C_7$ haloalkoxy groups are difluoro- or trifluoro-methoxy or ethoxy.

"Halogen" denotes chlorine, iodine, fluorine and bromine.

"$C_{3-10}$-cycloalkyl" denotes a monovalent saturated moiety, consisting of one, two or three carbon rings having 3 to 10 carbon atoms as ring members and includes but is not limited to cyclopropyl, cyclobutyl, cyclopentyl, cyclohexyl, cycloheptyl and polyspiro groups such as bicyclo[3.2.1]octane or adamantane as well as those groups specifically illustrated by the examples herein below.

The term "heteroatom" when used to describe atoms within a "heteroaryl" or "heterocycloalkyl" group (as defined below) refers to an atom selected from the group consisting of nitrogen, oxygen, and sulfur. In a heteroaryl or heterocycloalkyl with more than one heteroatom, the heteroatoms can be the same or different.

"Heteroaryl" means a monocyclic or bicyclic radical having at least one aromatic ring containing one, two, three or four ring heteroatoms, the remaining ring atoms being carbon, with the understanding that the attachment point of the radical to the remainder of the molecule is on the aromatic ring moiety containing the heteroatom(s). The heteroaryl ring may be optionally substituted as defined herein. Heteroaryls having 5 to 12 ring atoms and are referred to herein as "5- to 12-membered heteroaryl"s. Examples of such heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, furanyl, pyridyl, pyrrolyl, pyrazolyl, pyrimidyl, quinolinyl, isoquinolinyl, benzofurylbenzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, as well as those specifically illustrated by the examples herein below. Preferred heteroaryls have 5 or 6 ring atoms and are referred to herein as "5- to 6-membered heteroaryl"s. Examples of such 5- to 6-membered heteroaryls are [1,2,4]oxadiazolyl, indolyl, thiophenyl, pyridinyl as well as those specifically illustrated by the examples herein below. Also preferred are heteroaryls which have 5 to 10 ring atoms and are referred to herein as "5- to 10-membered heteroaryl"s. Examples of such 5- to 10-membered heteroaryls include [1,2,4]oxadiazolyl, thiophenyl, pyridinyl, quinolinyl as well as those specifically illustrated by the examples herein below.

In embodiments in which the heteroaryl moiety consists of a bicyclic ring, preferably one of the rings is a six-membered aromatic ring where the members are each carbon and the other ring is a 5- to 6-membered ring containing two oxygen atoms. Examples of such heteroaryl moieties include, but are not limited to, 2,3-dihydro-benzo[1,4]dioxinyl, 2,3-dihydro-benzofuranyl, benzodioxolyl, benzopyranyl, benzoxazinyl, benzoxazinonyl, benzopiperidinyl, benzopiperazinyl, benzopyrrolidinyl, benzomorpholinyl, as well as those specifically illustrated by the examples herein below.

"Heterocycloalkyl" means a monovalent saturated or partially unsaturated radical, consisting of one to three rings, incorporating one, two, or three or four heteroatoms, the remaining ring atoms being carbon, with the understanding that the attachment point of the radical to the remainder of the molecule is on the heterocyclic, saturated or partially saturated moiety. Heterocycloalkyls having 5 to 12 ring atoms and are referred to herein as "5- to 12-membered heterocycloalkyls. Preferably, the rings are three- to seven-membered. The heterocycloalkyl ring may be optionally substituted as defined herein. Examples of heterocycloalkyl radicals include, but are not limited to, optionally substituted piperidinyl, piperazinyl, homopiperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, quinuclidinyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, as well as those groups specifically illustrated by the examples herein below. Preferred 5- to 12-membered heterocycloalkyls are those having 5 to 10 ring atoms. Such heterocycloalkyls are termed "5- to 10-membered heterocycloalkyl"s. Examples of such heterocycloalkyls are tetrahydrofuranyl and tetrahydropyranyl. Also preferred are heterocycloalkyls having 5 to 6 ring atoms. Such heterocycloalkyls are termed "5- to 6-membered heterocycloalkyls".

"Oxo" denotes a =O group.

"Cyano" denotes a —CN group.

"Pharmaceutically-acceptable", when used to describe a salt, acid, excipient, or other compound, means that the compound is useful in preparing a pharmaceutical composition that is generally safe, non-toxic, and neither biologically nor otherwise undesirable and includes compounds which are acceptable for veterinary as well as human pharmaceutical use.

A "pharmaceutically-acceptable salt" of a compound means a salt that is pharmaceutically-acceptable, as defined herein, and that possesses the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, as well as those groups specifically illustrated by the examples herein below.

In a preferred embodiment of the present invention, the compound is a compound of formula I, or a pharmaceutically-acceptable salt thereof, in which A is selected from the group consisting of:

aryl, optionally substituted by at least one substituent, each substituent being independently selected from the group consisting of: halogen, cyano and $C_{1-6}$-alkyl substituted by cyano; and 5- to 6-membered heteroaryl, for example pyridinyl.

In a certain embodiment of the invention, the compound is a compound of formula I, or a pharmaceutically-acceptable salt thereof, in which $R^1$ is $C_{1-6}$-alkyl optionally substituted by at least one substituent, each substituent being independently selected from the group consisting of: halogen and $C_{1-6}$-alkoxy. Examples of such compounds include:

N-trans(4-{2-[4-(4-Fluoro-phenoxy)-piperidin-1-yl]-ethyl}-cyclohexyl)-3-methoxy-propionamide;

N-trans(4-{2-[4-(4-Fluoro-phenoxy)-piperidin-1-yl]-ethyl}-cyclohexyl)-acetamide;

N-trans(4-{2-[4-(2-Chloro-4-fluoro-phenoxy)-piperidin-1-yl]-ethyl}-cyclohexyl)-3-methoxy-propionamide;

N-trans(4-{2-[4-(2-Chloro-4-fluoro-phenoxy)-piperidin-1-yl]-ethyl}-cyclohexyl)-propionamide;

N-trans(4-{2-[4-(2-Chloro-4-fluoro-phenoxy)-piperidin-1-yl]-ethyl}-cyclohexyl)-acetamide;

N-trans(4-{2-[4-(2,4-Difluoro-phenoxy)-piperidin-1-yl]-ethyl}-cyclohexyl)-acetamide;

N-trans(4-{2-[4-(2-Cyano-4-fluoro-phenoxy)-piperidin-1-yl]-ethyl}-cyclohexyl)-3-methoxy-propionamide;

N-trans(4-{2-[4-(2-Cyano-4-fluoro-phenoxy)-piperidin-1-yl]-ethyl}-cyclohexyl)-acetamide;

N-trans(4-{2-[4-(2-Cyano-4-fluoro-phenoxy)-piperidin-1-yl]-ethyl}-cyclohexyl)-2,2,2-trifluoro-acetamide; trans N-(4-{2-[4-(2,3-Dichloro-phenoxy)-piperidin-1-yl]-ethyl}-cyclohexyl)-3-methoxy-propionamide;
N-trans(4-{2-[4-(2,3-Dichloro-phenoxy)-piperidin-1-yl]-ethyl}-cyclohexyl)-acetamide;
N-trans(4-{2-[4-(2,6-Dichloro-4-fluoro-phenoxy)-piperidin-1-yl]-ethyl}-cyclohexyl)-3-methoxy-propionamide;
N-trans(4-{2-[4-(2,6-Dichloro-4-fluoro-phenoxy)-piperidin-1-yl]-ethyl}-cyclohexyl)-acetamide;
N-trans(4-{2-[4-(2,4,5-Trifluoro-phenoxy)-piperidin-1-yl]-ethyl}-cyclohexyl)-acetamide;
N-trans(4-{2-[4-(2-Cyano-phenoxy)-piperidin-1-yl]-ethyl}-cyclohexyl)-acetamide;
N-trans(4-{2-[4-(4-Chloro-2-cyano-phenoxy)-piperidin-1-yl]-ethyl}-cyclohexyl)-acetamide;
N-trans(4-{2-[4-(3-Chloro-2-cyano-phenoxy)-piperidin-1-yl]-ethyl}-cyclohexyl)-acetamide;
N-trans(4-{2-[4-(3-Chloro-4-fluoro-phenoxy)-piperidin-1-yl]-ethyl}-cyclohexyl)-acetamide;
N-trans(4-{2-[4-(2,3,4-Trifluoro-phenoxy)-piperidin-1-yl]-ethyl}-cyclohexyl)-acetamide;
N-(trans-4-{2-[4-(Pyridin-3-yloxy)-piperidin-1-yl]-ethyl}-cyclohexyl)-acetamide; and pharmaceutically-acceptable salts of such compounds.

In another embodiment of the invention, the compound is a compound of formula I, or a pharmaceutically-acceptable salt thereof, in which $R^1$ is $C_{3-10}$-cycloalkyl optionally substituted by at least one $R^a$, wherein each $R^a$ is independently a $C_{1-6}$-alkyl. Examples of such compounds include:
Cyclopropanecarboxylic acid trans(4-{2-[4-(4-fluoro-phenoxy)-piperidin-1-yl]-ethyl}-cyclohexyl)-amide;
Cyclopropanecarboxylic acid trans(4-{2-[4-(2-chloro-4-fluoro-phenoxy)-piperidin-1-yl]-ethyl}-cyclohexyl)-amide;
Cyclobutanecarboxylic acid trans(4-{2-[4-(2-cyano-4-fluoro-phenoxy)-piperidin-1-yl]-ethyl}-cyclohexyl)-amide;
Cyclopropanecarboxylic acid trans(4-{2-[4-(2-cyano-4-fluoro-phenoxy)-piperidin-1-yl]-ethyl}-cyclohexyl)-amide;
2-Methyl-cyclopropanecarboxylic acid trans(4-{2-[4-(2-cyano-4-fluoro-phenoxy)-piperidin-1-yl]-ethyl}-cyclohexyl)-amide;
Cyclobutanecarboxylic acid trans(4-{2-[4-(2,3-dichloro-phenoxy)-piperidin-1-yl]-ethyl}-cyclohexyl)-amide;
Cyclobutanecarboxylic acid trans(4-{2-[4-(2,6-dichloro-4-fluoro-phenoxy)-piperidin-1-yl]-ethyl}-cyclohexyl)-amide;
Cyclobutanecarboxylic acid trans(4-{2-[4-(2,4,6-trifluoro-phenoxy)-piperidin-1-yl]-ethyl}-cyclohexyl)-amide;
Cyclobutanecarboxylic acid trans(4-{2-[4-(2,4,5-trifluoro-phenoxy)-piperidin-1-yl]-ethyl}-cyclohexyl)-amide;
2-Methyl-cyclopropanecarboxylic acid trans(4-{2-[4-(2,4,5-trifluoro-phenoxy)-piperidin-1-yl]-ethyl}-cyclohexyl)-amide;
Cyclopropanecarboxylic acid trans(4-{2-[4-(4-cyano-phenoxy)-piperidin-1-yl]-ethyl}-cyclohexyl)-amide; and pharmaceutically-acceptable salts of such compounds.

In another embodiment of the invention, the compound is a compound of formula I, or a pharmaceutically-acceptable salt thereof, in which $R^1$ is a 5- to 12-membered heterocycloalkyl. Examples of such compounds include:
Tetrahydro-pyran-4-carboxylic acid trans(4-{2-[4-(4-fluoro-phenoxy)-piperidin-1-yl]-ethyl}-cyclohexyl)-amide;
Tetrahydro-pyran-4-carboxylic acid trans(4-{2-[4-(2-chloro-4-fluoro-phenoxy)-piperidin-1-yl]-ethyl}-cyclohexyl)-amide;
Tetrahydro-pyran-4-carboxylic acid trans(4-{2-[4-(2,4-difluoro-phenoxy)-piperidin-1-yl]-ethyl}-cyclohexyl)-amide;
Tetrahydro-pyran-4-carboxylic acid trans(4-{2-[4-(2-cyano-4-fluoro-phenoxy)-piperidin-1-yl]-ethyl}-cyclohexyl)-amide;
Tetrahydro-pyran-4-carboxylic acid trans(4-{2-[4-(2,3-dichloro-phenoxy)-piperidin-1-yl]-ethyl}-cyclohexyl)-amide;
Tetrahydro-furan-2-carboxylic acid trans(4-{2-[4-(2,6-dichloro-4-fluoro-phenoxy)-piperidin-1-yl]-ethyl}-cyclohexyl)-amide;
Tetrahydro-pyran-4-carboxylic acid trans(4-{2-[4-(2,6-dichloro-4-fluoro-phenoxy)-piperidin-1-yl]-ethyl}-cyclohexyl)-amide;
Tetrahydro-furan-2-carboxylic acid trans(4-{2-[4-(2,4,6-trifluoro-phenoxy)-piperidin-1-yl]-ethyl}-cyclohexyl)-amide;
Tetrahydro-pyran-4-carboxylic acid trans(4-{2-[4-(2,4,5-trifluoro-phenoxy)-piperidin-1-yl]-ethyl}-cyclohexyl)-amide;
Tetrahydro-pyran-4-carboxylic acid trans(4-{2-[4-(4-chloro-2-cyano-phenoxy)-piperidin-1-yl]-ethyl}-cyclohexyl)-amide; and pharmaceutically-acceptable salts of such compounds.

In another embodiment of the invention, the compound is a compound of formula I, or a pharmaceutically-acceptable salt thereof, in which $R^1$ is aryl optionally substituted by at least one $R^a$, wherein each $R^a$ is independently selected from the group consisting of: halogen, $C_{1-6}$-alkoxy, $—S(O)_2—C_{1-6}$-alkyl, and 5- to 6-membered heteroaryl optionally substituted by $C_{1-6}$-alkyl. Examples of such compounds include:
4-Chloro-N-trans(4-{2-[4-(4-fluoro-phenoxy)-piperidin-1-yl]-ethyl}-cyclohexyl)-benzamide;
N-trans(4-{2-[4-(4-Fluoro-phenoxy)-piperidin-1-yl]-ethyl}-cyclohexyl)-3-(5-methyl-[1,2,4]oxadiazol-3-yl)-benzamide;
N-trans(4-{2-[4-(4-Fluoro-phenoxy)-piperidin-1-yl]-ethyl}-cyclohexyl)-4-methanesulfonyl-benzamide;
N-trans(4-{2-[4-(2-Chloro-4-fluoro-phenoxy)-piperidin-1-yl]-ethyl}-cyclohexyl)-4-methanesulfonyl-benzamide;
4-Chloro-N-trans(4-{2-[4-(2-chloro-4-fluoro-phenoxy)-piperidin-1-yl]-ethyl}-cyclohexyl)-benzamide;
N-trans(4-{2-[4-(2-Chloro-4-fluoro-phenoxy)-piperidin-1-yl]-ethyl}-cyclohexyl)-3-(5-methyl-[1,2,4]oxadiazol-3-yl)-benzamide;
4-Chloro-N-trans(4-{2-[4-(2-cyano-4-fluoro-phenoxy)-piperidin-1-yl]-ethyl}-cyclohexyl)-benzamide;
N-trans(4-{2-[4-(2-Cyano-4-fluoro-phenoxy)-piperidin-1-yl]-ethyl}-cyclohexyl)-4-methoxy-benzamide;
4-Methoxy-N-trans(4-{2-[4-(2,4,6-trifluoro-phenoxy)-piperidin-1-yl]-ethyl}-cyclohexyl)-benzamide;
4-Chloro-N-trans(4-{2-[4-(2,4,6-trifluoro-phenoxy)-piperidin-1-yl]-ethyl}-cyclohexyl)-benzamide;
4-Methoxy-N-trans(4-{2-[4-(2,4,5-trifluoro-phenoxy)-piperidin-1-yl]-ethyl}-cyclohexyl)-benzamide;
4-Chloro-N-trans(4-{2-[4-(2,4,5-trifluoro-phenoxy)-piperidin-1-yl]-ethyl}-cyclohexyl)-benzamide;
N-trans(4-{2-[4-(2-Cyano-phenoxy)-piperidin-1-yl]-ethyl}-cyclohexyl)-4-ethoxy-benzamide;

and pharmaceutically-acceptable salts of such compounds.

In another embodiment of the invention, the compound is a compound of formula I, or a pharmaceutically-acceptable salt thereof, in which $R^1$ is a 5- to 12-membered heteroaryl. Examples of such compounds include:

1H-Indole-2-carboxylic acid trans(4-{2-[4-(4-fluoro-phenoxy)-piperidin-1-yl]-ethyl}-cyclohexyl)-amide;
Quinoline-4-carboxylic acid trans(4-{2[4-(2-chloro-4-fluoro-phenoxy)-piperidin-1-yl]-ethyl}-cyclohexyl)-amide;
Quinoline-6-carboxylic acid trans(4-{2-[4-(2,4-difluoro-phenoxy)-piperidin-1-yl]-ethyl}-cyclohexyl)-amide;
Quinoline-4-carboxylic acid trans(4-{2-[4-(2,4-difluoro-phenoxy)-piperidin-1-yl]-ethyl}-cyclohexyl)-amide;
Thiophene-2-carboxylic acid trans(4-{2-[4-(2-cyano-4-fluoro-phenoxy)-piperidin-1-yl]-ethyl}-cyclohexyl)-amide;
Thiophene-2-carboxylic acid trans(4-{2-[4-(2,3-dichloro-phenoxy)-piperidin-1-yl]-ethyl}-cyclohexyl)-amide;
Thiophene-2-carboxylic acid trans(4-{2-[4-(2,6-dichloro-4-fluoro-phenoxy)-piperidin-1-yl]-ethyl}-cyclohexyl)-amide;
Thiophene-2-carboxylic acid trans(4-{2-[4-(2,4,5-trifluoro-phenoxy)-piperidin-1-yl]-ethyl}-cyclohexyl)-amide;
Thiophene-2-carboxylic acid trans(4-{2-[4-(4-cyano-2-fluoro-phenoxy)-piperidin-1-yl]-ethyl}-cyclohexyl)-amide;
Quinoline-4-carboxylic acid trans(4-{2-[4-(2-cyano-phenoxy)-piperidin-1-yl]-ethyl}-cyclohexyl)-amide;
Quinoline-4-carboxylic acid trans(4-{2-[4-(2-chloro-4-fluoro-phenoxy)-3-hydroxy-piperidin-1-yl]-ethyl}-cyclohexyl)-amide;
Quinoline-4-carboxylic acid trans(4-{2-[(3R,4R)-4-(2-chloro-4-fluoro-phenoxy)-3-hydroxy-piperidin-1-yl]-ethyl}-cyclohexyl)-amide;
Quinoline-4-carboxylic acid trans(4-{2-[(3S,4S)-4-(2-chloro-4-fluoro-phenoxy)-3-hydroxy-piperidin-1-yl]-ethyl}-cyclohexyl)-amide;
Quinoline-4-carboxylic acid trans(4-{2-[4-(4-fluoro-phenoxy)-piperidin-1-yl]-ethyl}-cyclohexyl)-amide;
Quinoline-4-carboxylic acid trans(4-{2-[4-(2,3-dichloro-phenoxy)-piperidin-1-yl]-ethyl}-cyclohexyl)-amide;
Quinoline-4-carboxylic acid trans(4-{2-[4-(3,4-dichloro-phenoxy)-piperidin-1-yl]-ethyl}-cyclohexyl)-amide;
Quinoline-4-carboxylic acid trans(4-{2-[4-(pyridin-4-yloxy)-piperidin-1-yl]-ethyl}-cyclohexyl)-amide; and pharmaceutically-acceptable salts of such compounds.

In another embodiment of the invention, the compound is a compound of formula I, or a pharmaceutically-acceptable salt thereof, in which $R^1$ is $-NR^bR^c$ wherein $R^b$ is hydrogen and $R^c$ is independently selected from the group consisting of hydrogen and aryl optionally substituted by at least one $R^a$, wherein each $R^a$ is independently selected from the group consisting of halogen and $C_{1-6}$-alkyl. Examples of such compounds include:

1-(4-Chloro-phenyl)-3-trans(4-{2-[4-(4-fluoro-phenoxy)-piperidin-1-yl]-ethyl}-cyclohexyl)-urea;
1-trans(4-{2-[4-(4-Fluoro-phenoxy)-piperidin-1-yl]-ethyl}-cyclohexyl)-3-p-tolyl-urea;
1-trans(4-{2-[4-(2-Chloro-4-fluoro-phenoxy)-piperidin-1-yl]-ethyl}-cyclohexyl)-3-p-tolyl-urea;
1-trans(4-{2-[4-(2-Chloro-4-fluoro-phenoxy)-piperidin-1-yl]-ethyl}-cyclohexyl)-3-(4-chloro-phenyl)-urea; and pharmaceutically-acceptable salts of such compounds.

A further aspect of the present invention is a process for the preparation of a compound of the present invention.

In an embodiment of the present invention, such a process involves reacting a compound of the formula II:

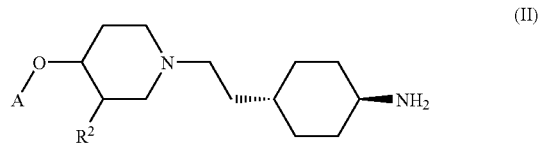

(II)

with an acid of the formula III:

$HOOCR^1$ (III)

in the presence of a coupling reagent such as O-(benzotriazol-1-yl)-N,N,N',N'-tetramethyluronium tetrafluoroborate (TBTU) in a suitable solvent like, e.g. dimethylformamide (DMF) or dioxane in the presence of a base (e.g. triethylamine or diisopropylethylamine) to obtain a compound of the formula (I).

In the above formulas, $R^1$ is selected from the group consisting of:

$C_{1-6}$-alkyl optionally substituted by at least one substituent, each of said substituent being independently selected from the group consisting of: halogen, $C_{1-6}$-alkoxy, and aryl optionally substituted by halogen;
$C_{3-10}$-cycloalkyl optionally substituted by one or more $R^a$;
5- to 12-membered heterocycloalkyl optionally substituted by one or more $R^a$;
aryl optionally substituted by one or more $R^a$; and
5- to 12-membered heteroaryl optionally substituted by one or more $R^a$.

A, $R^a$, and $R^2$ are as defined herein above.

In another embodiment of the present invention, the process involves reacting a compound of formula II

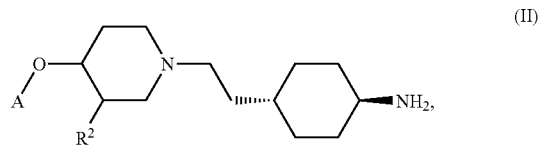

(II)

wherein A, $R^a$, and $R^2$ are as defined above and $R^1$ is $-NR^bR^c$, wherein $R^b$ is hydrogen or $C_{1-6}$-alkyl and wherein $R^c$ is aryl optionally substituted by one or more $R^a$, with an isocyanate or a reactive intermediate such as para nitro carbamate in a suitable solvent like, e.g. dimethylformamide (DMF) or acetonitrile in the presence of a base (e.g. triethylamine or diisopropylethylamine) to obtain a compound of the formula (I).

If desired, the compound as obtained by either of the above processes may be converted into a pharmaceutically-acceptable acid addition salt.

The preparation of compounds of formula (I) of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given herein below, by methods described in references cited in the description or in the examples, or by methods known in the art.

In the following schemes and unless stated otherwise, A, $R^1$, $R^2$, $R^b$, and $R^c$ are as described hereinabove.

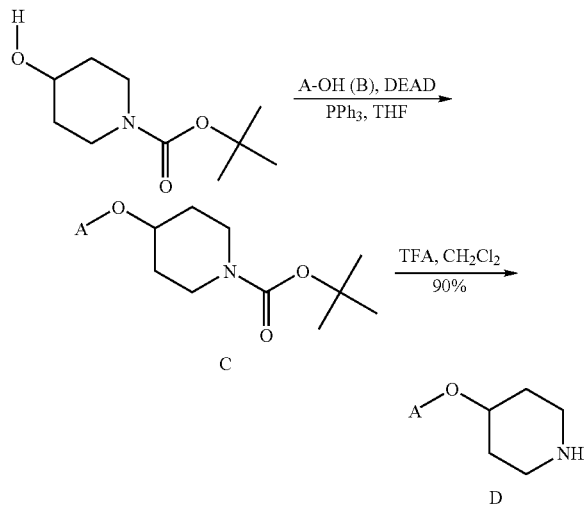

Scheme 1

The piperidin-4-yloxy-aryl or heteroaryl compound can be prepared according to scheme 1. The syntheses of ethers are widely described in literature and the procedures are known to those in the art (for reaction conditions described in literature affecting such reactions see for example: Comprehensive Organic Transformations: A Guide to Functional Group Preparations, 2nd Edition, Richard C. Larock. John Wiley & Sons, New York, 1999). The transformation can be effected by employing reaction conditions which are commonly utilised in the so called "Mitsunobu reaction" which is known to those in the art and widely described (Hughes, David L. The Mitsunobu reaction. Organic Reactions, John Wiley & Sons, New York, 1992, 42, 335-656). It has been found convenient to couple the commercially available 4-hydroxy-piperidine-1-carboxylic acid tert-butyl ester with aryl or heteroaryl alcohols of formula B (either commercially available or accessible by methods described in references or by methods known in the art; as appropriate) under conditions employing a phosphine, for example a trialkylphosphine such as tributylphosphine ($(n-Bu)_3$, P) or a triarylphosphine such as triphenylphosphine ($PPh_3$) and the like, and a diazo-compound, for example diethyl-azodicarboxylate (DEAD), diisopropyl-azodicarboxylate (DIAD) (optionally polymer bound), tetramethyl azodicarboxamide and the like, in a solvent commonly used in such transformations like tetrahydrofuran (THF), toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. It has been found convenient to carry out the reaction at ambient temperature. The time required for the reaction may also vary widely, depending on many factors, notably the reaction temperature and the nature of the reagents. However, a period of from few hours to one day will usually suffice to yield the compounds of formula C. The protecting group can be removed under conditions known for those skilled in the art (e.g. treatment with an acid such as trifluoroacetic acid in a suitable solvent such as dichloromethane) as described on scheme 1.

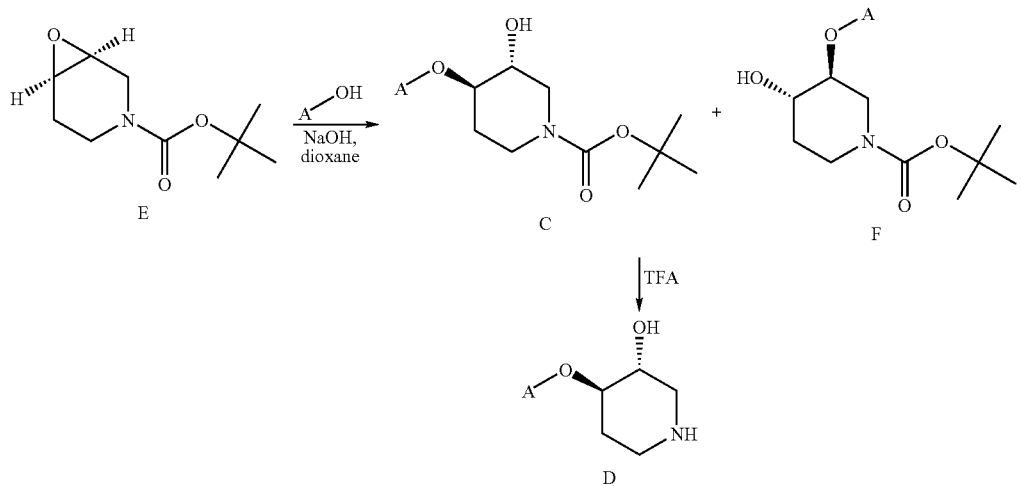

Scheme 2

Aryl or heteroaryl piperidin-4-yloxy compounds with $R^2$=OH can be prepared according to scheme 2 with opening of rac-cis-7-oxa-3-aza-bicyclo[4.1.0]heptane-3-carboxylic acid tert-butyl ester using the aryl or heteroaryl hydroxy derivative A-OH in the presence of sodium hydroxide heating in a solvent like dioxane. Removal of the protecting group in conditions as the ones described on scheme 1 provides compounds of formula D were $R^2$=OH

Scheme 3

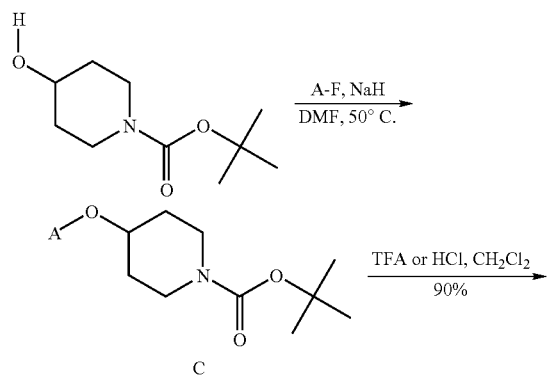

Also aryl or heteroaryl piperidin-4-yloxy compounds of structure D containing an electron withdrawing group such as nitrile in ortho or para position can be prepared according to scheme 3 by an nucleophilic aromatic substitution of the corresponding fluoroaryl compound (A-F) with 4-hydroxy-piperidine-1-carboxylic acid tert-butyl ester after deprotonation with a base such as NaH in a polar solvent such as DMF. Removal of the protective group in conditions as the ones described in scheme 1 provides compounds of formula D.

Scheme 4

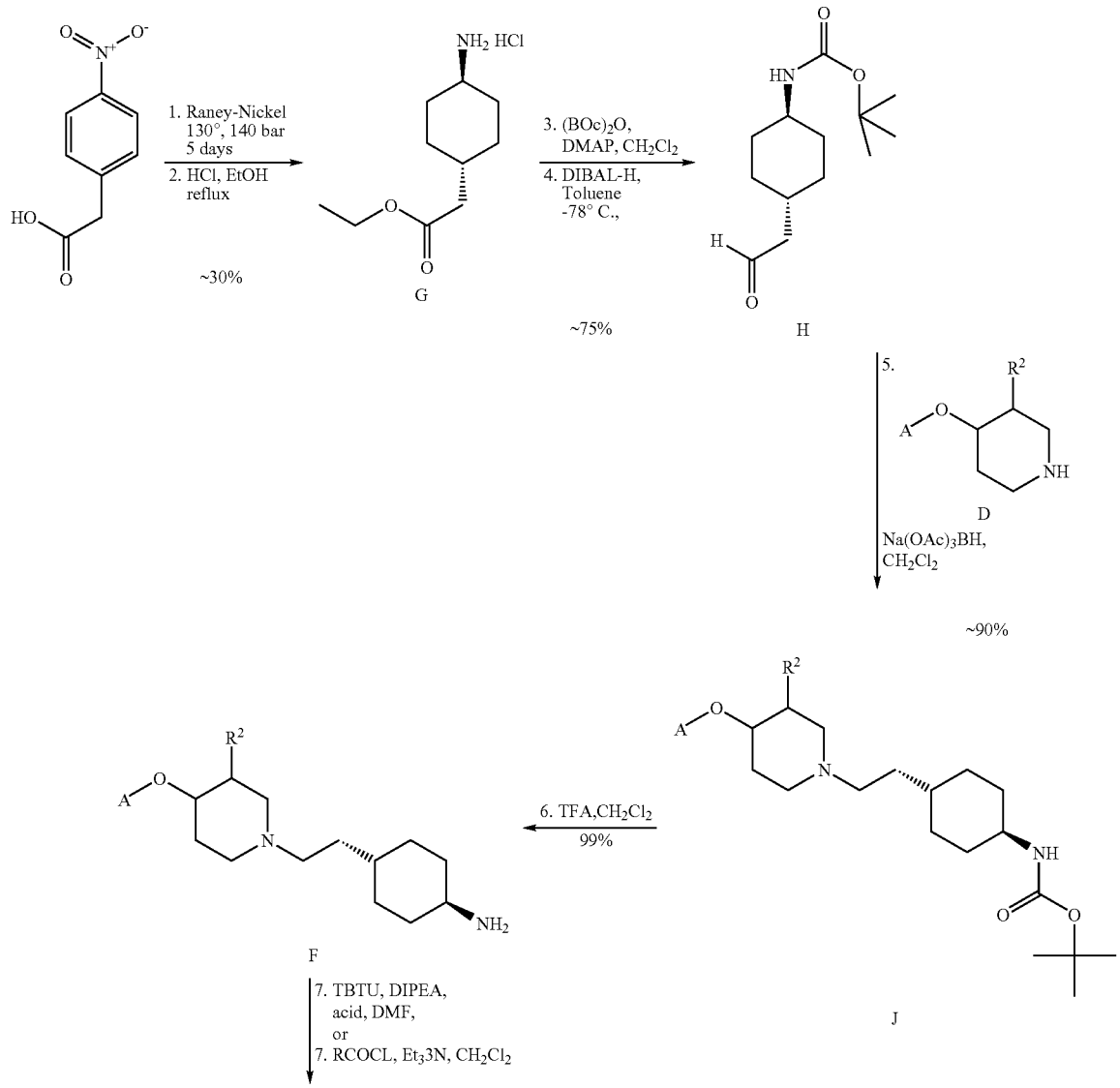

-continued

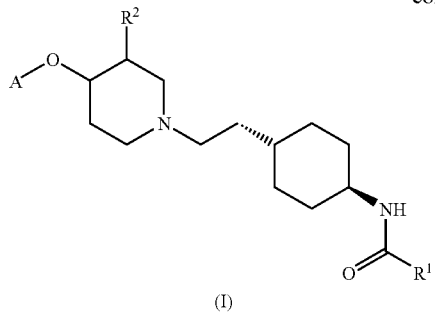

(I)

(Heteroaryl or phenoxy-piperidin-1-yl)trans-ethyl-cyclohexyl-amides or trans-1,4-cyclohexyl ethyl derivates of formula (I) can be prepared as depicted in scheme 4 starting from 4-nitro-phenylacetic acid. 4-nitro-phenylacetic acid is hydrogenated using Raney nickel as a catalyst. The hydrogenation with nickel leads preferentially to the desired trans-isomer (according to Wustrow et. al. J of Med. Chem., 1998, 41, 760-771). The ethyl ester can be prepared according to methods known to those skilled in the art and described in the mentioned literature (e.g by treatment with ethanol on the presence of an acid such as HCl) and the desired pure diastereoisomer can be resolved from the cis/trans mixture by crystallization as the HCl salt. trans-Amino ester chloride G is obtained. Reaction with tert-butyl dicarbonate ((BOc)$_2$O) in the presence of a base like triethylamine and a catalyst like dimethylaminopyridine (DMAP) and reduction with diisobutylaluminium hydride (DIBAL-H) in an appropriate solvent such as e.g. toluene at −78° C. gives the aldehyde H which can be used without purification on the next step. Reductive amination of aldehyde H with aryl or heteroaryl piperidin-4-yloxy compounds of formula D (which is either commercially available or can be made by methods described in references, by methods described in this patent or by methods known in the art) in the presence of a solvent like 1,2-dichloroethane and a reducing agent such as sodium triacetoxy borohydride (Na(OAc)$_3$BH) yields intermediate J. Removal of the tert-butyl acetate protective group under acidic conditions, for example, using trifluoroacetic acid (TFA), in a suitable solvent, such as tetrahydrofuran (THF), yields the trans-amino cyclohexyl ethyl intermediate K (usually the TFA salt). The coupling of the amine intermediate K with carboxylic acids (either commercially available or accessible by methods described in references or by methods known in the art) is widely described in the literature (e.g. Comprehensive Organic Transformations: A Guide to Functional Group Preparations, 2nd Edition, Richard C. Larock. John Wiley & Sons, New York, N.Y. 1999) and can be accomplished by employing coupling reagents such as, e.g. N,N-carbonyldiimidazole (CDI) or O-(benzotriazol-1-yl)-N,N,N',N'-tetramethyluronium tetrafluoroborate (TBTU) in a suitable solvent like e.g. dimethylformamide (DMF) or dioxane in the presence of a base (e.g. triethylamine or diisopropylethylamine) to yield compounds of formula (I). In other cases an acid chloride (RCOCl wherein R is an organic radical group) can also be used in the presence of a base (e.g. triethylamine (Et$_3$N) or diisopropylethylamine (DIPEA)) in a solvent like dichloromethane.

Scheme 5

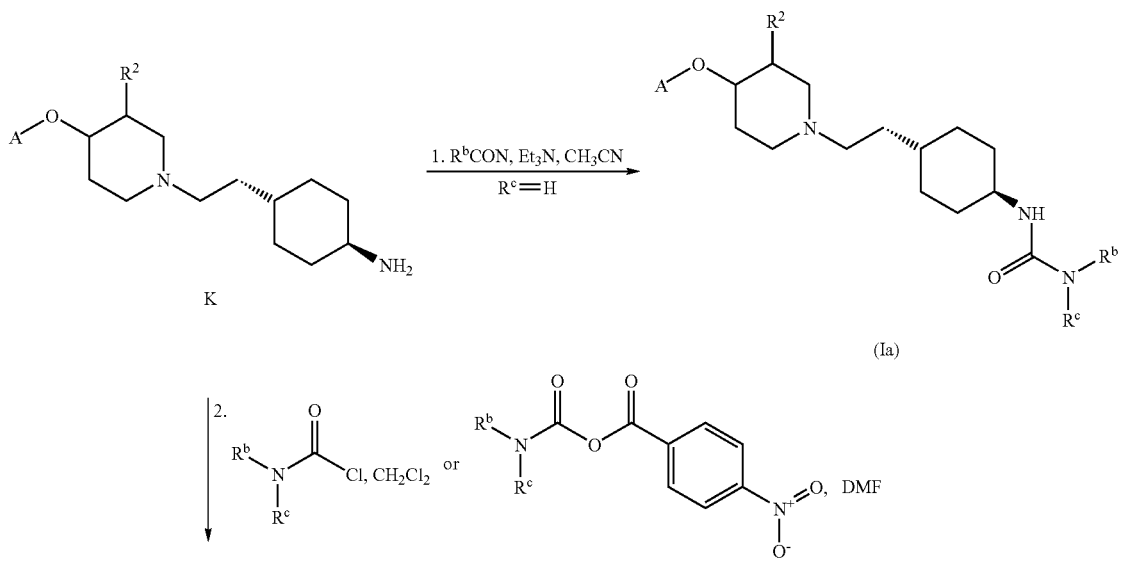

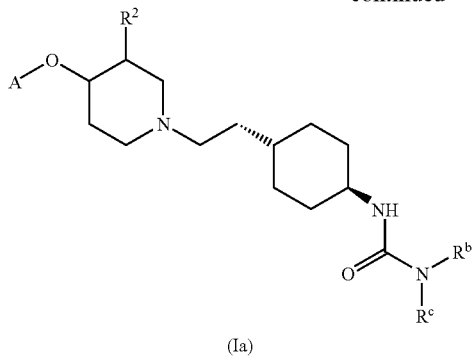

(Ia)

In other embodiments the intermediate K can also react with an isocyanate ($R^b$CON) (when $R^c$ is hydrogen) or a reactive intermediate (when $R^c$ is other than hydrogen) such as an appropriate acid chloride or a para nitro carbamate prepared by methods known in the art on the presence of a suitable solvent like, e.g. acetonitrile or dichloromethane in the presence of a base (e.g. triethylamine or diisopropylethylamine) to obtain a compound of the formula (Ia) as described on scheme 5 above.

Scheme 6

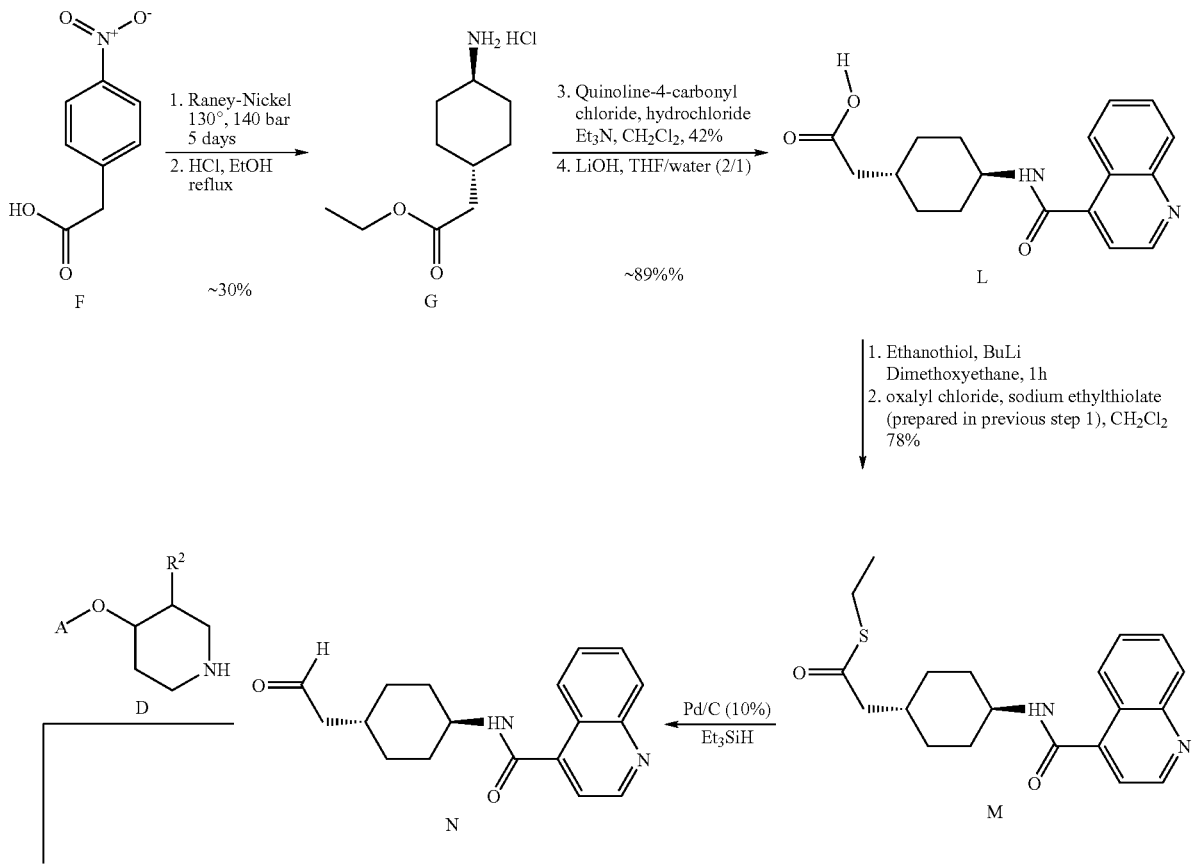

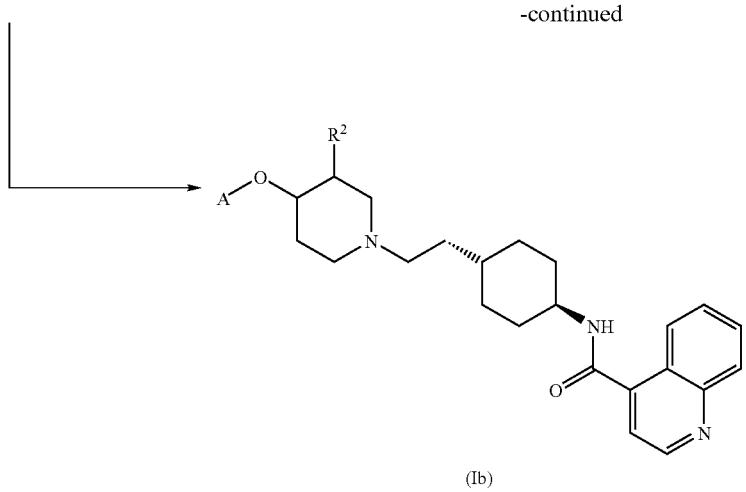

In some embodiments the aryl or heteroaryl piperidin-4-yloxy compounds of formula D can be coupled in a reductive amination step with a more elaborated aldehyde N according to scheme 6. In some cases the quinoline-4-carboxylic acid [4-(2-oxo-ethyl)-cyclohexyl]-amide was used. The preparation of quinoline-4-carboxylic acid [4-(2-oxo-ethyl)-cyclohexyl]-amide N is described on scheme 6 starting from 4-nitro-phenylacetic acid F that is hydrogenated as already described on scheme 3 using Raney nickel and preparing the trans-amino ethyl ester chloride G as already also described on scheme 3. In this case instead of reacting G with tert-butyl dicarbonate, the amine hydrochloride can be reacted with quinoline-4-carbonyl chloride in the presence of a base such as triethylamine in a solvent such as dichloromethane to obtain trans-{4-[(quinoline-4-carbonyl)-amino]-cyclohexyl}-acetic acid ethyl ester. Hydrolysis of the ester function under acidic or basic conditions such as lithium hydroxide in a solvent mixture such as tetrahydrofuran (THF):water gives the corresponding carboxylic acid L. The preparation of acid derivatives in order to make reductions is known in literature (e.g. T. Fukuyama et. al., Synthesis 2000, 8, 1121-1123). In this case reaction of the carboxylic acid with sodium ethylthiolate prepared previously from ethanothiol and a base such as butyllithium (BuLi) in a solvent such as dimethoxyethane yields trans-{4-[(quinoline-4-carbonyl)-amino]-cyclohexyl}-thioacetic acid S-ethyl ester M that can be reduced with palladium on charcoal (Pd/C) and triethylsilane (Et$_3$SiH) in a solvent mixture like acetone/methylenehloride (1:1) to obtain the desired trans-quinoline-4-carboxylic acid [4-(2-oxo-ethyl)-cyclohexyl]-amide N that can be used in a reductive amination using a reducing agent such as sodium triacetoxy borohydride (Na(OAc)$_3$BH) in a solvent such as dichloromethane to obtain directly trans-quinoline-4-carboxylic acid (4-{2-[(heteroaryl or phenoxy)-piperidin-1-yl]-ethyl}-cyclohexyl)-amide (Ib).

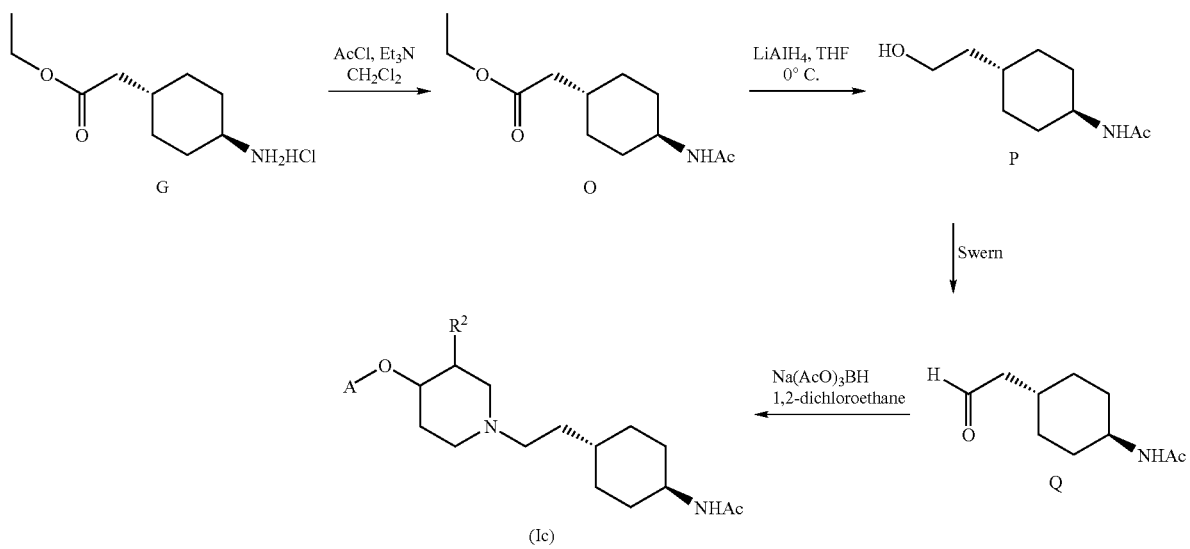

Acetic acid amide derivatives of structure (Ic) can be conveniently prepared according to scheme 7 starting from compound G. The reaction sequence involves in a first step the treatment of compound G with acetyl chloride (AcCl) in presence of a base such as triethylamine ($Et_3N$) in a solvent such as $CH_2Cl_2$ to obtain a compound of formula O. Reduction with a reagent such as $LiAlH_4$ in a solvent such as $CH_2Cl_2$ at 0° C. provides a compound of formula P. Among several oxidation conditions known in the literature, the Swern oxidation (A. Mancuso, D. Swern, Synthesis 1981, 165-185) of alcohol P provides intermediate Q. Reaction of aldehyde Q with an appropriate substituted piperidine in the presence of a reducing agent such as sodium triacetoxy borohydride ($Na(AcO)_3BH$) in a solvent such as 1,2-dichloroethane provides compounds of formula (Ic).

The compounds of formula I and pharmaceutically-acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I, or a pharmaceutically-acceptable salt thereof, and a therapeutically inert excipient are also an object of the present invention, as is a process for the production of such a composition which comprises bringing one or more compounds of formula I, or pharmaceutically-acceptable salts thereof, and, if desired, one or more other therapeutically valuable substances into a galenical dosage form together with one or more therapeutically inert carriers such as those described above.

The compound of the present invention may be used in a method for treating or preventing cognitive disorders, drug addiction, depression, anxiety, drug dependence, dementias, memory impairment, psychotic disorders comprising schizophrenia, schizoaffective disorders, bipolar disease, mania, psychotic depression, or psychoses comprising paranoia and delusions. In such a method, the compound is administered to a patient in a therapeutically-effective amount. A "therapeutically-effective amount", as used herein, means the amount of the subject compound or combination that will elicit the biological or medical response of a tissue, system, animal or human that is being sought by the researcher, veterinarian, medical doctor or other clinician. The amount can vary within wide limits and will, of course, be fitted to the individual requirements in each particular case. In general, the effective dosage for oral or parenteral administration of the compound is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

EXAMPLES

The following examples are provided to further elucidate the invention.

Example 1

1H-Indole-2-carboxylic acid trans-(4-{2-[4-(4-fluoro-phenoxy)-piperidin-1-yl]-ethyl}-cyclohexyl)-amide Intermediate C 1.1 4-(4-Fluoro-phenoxy)-piperidine 1-carboxylic acid tert-butyl ester To a solution of triphenyl phosphine (7.7 g, 29 mmol), in tetrahydrofuran (40 mL), diethylazodicarboxylate (5.12 g, 29 mmol) was added and the solution was stirred for 20 minutes. 4-Fluorophenol (3 g, 27 mmol) was added and the mixture was stirred for another 20 minutes at 0° C. N—Boc-4-hydroxypiperidine (5.9 g, 29 mmol) was added dissolved in tetrahydrofuran (20 mL) and the mixture was stirred at room temperature overnight. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (1:0 to 1:1) to give 4.8 g (60%) of the product as a white solid. MS (m/e): 296.3 (M–H$^+$).

Intermediate D 1.2 4-(4-Fluoro-phenoxy)-piperidine 2 g (7 mmol) of 4-(4-fluoro-phenoxy)-piperidine 1-carboxylic acid tert-butyl ester was solvated in dichloromethane (12 mL) and trifluoroacetic acid was added at 0° C. (6.17 mL, 54 mmol). The mixture was stirred at room temperature overnight. NaHCO$_3$ was slowly added until pH 9 and the mixture extracted 3 times with dichloromethane and ethyl acetate. The solvent was evaporated to yield 1.81 g (58.5 mmol, 85%) of a white solid that was used without purification on the next steps. MS (m/e): 196.3 (M+H$^+$).

1.3 trans-(4-{2-[4-(4-Fluoro-phenoxy)-piperidin-1-yl]-ethyl}-cyclohexyl)-carbamic acid tert-butyl ester Intermediate G trans-(4-Amino-cyclohexyl)-acetic acid ethyl ester Step 1.

(4-Nitro-phenyl)-acetic acid (50 g, 276 mmol) was added to a stirred solution of 22.08 g of 50% sodium hydroxide solution in 450 mL deionizated water. The clear yellow solution was transferred into a high-pressure autoclave that it charged with 30 g (511 mmol) of water-wet sponge nickel catalyst. The autoclave was sealed, flushed with nitrogen and then pressurized to 115 bar with hydrogen. The reaction mixture was stirred and heated to 125° C. for 48 h. At that time the autoclave was cooled, vented and charged under nitrogen with another 30 g (511 mmol) of the sponge nickel catalyst. The autoclave was flushed again with nitrogen and then pressurized to 115 bar and the vessel was heated to 130° C. while stirring (a maximum pressure of 130 bars was observed). Hydrogenation was continued for 5 days to 130° C. The autoclave was then cooled, vented and flushed with nitrogen and the contents are removed and filtered through filter aid to remove catalyst. After removal of the solvent 74 g of crude material was obtained. The intermediated was used directly in the next step without purification. MS (m/e): 158.3 (M+H$^+$).

Step 2

A solution of trans-(4-amino-cyclohexyl)-acetic acid (74 g, 476 mmol) was adjusted to pH 5 with 25% HCl. The mixture was evaporated to dryness and dried under vacuum overnight. The residue was suspended in 146 mL of a 6.5 N ethanolic HCl solution and 0.6 L of ethanol was added to the mixture. After 4 hours refluxing, the mixture was cooled and filtered and the filtrate was concentrated to dryness under vacuum. The residue was dissolved in ethanol, treated with ether and cooled overnight in the refrigerator to give trans-(4-amino-cyclohexyl)-acetic acid ethyl ester hydrochloride (19.7 g, 32% on the two steps) as a white solid which was filtered and dried under vacuum. MS (m/e): 186.1 (M+H$^+$).

Intermediate H

Step 1 trans-(4-tert-Butoxycarbonylamino-cyclohexyl)-acetic acid ethyl ester

To a solution of trans-(4-amino-cyclohexyl)-acetic acid ethyl ester (1.28 g, 7 mmol), in dichloromethane (15 mL), di-tert-butyl-dicarbonate (2.26 g, 10 mmol), triethylamine (0.699 mL, 7 mmol) and 4-dimethylaminopyridine (0.042 mL, 0.35 mmol) were added. The mixture was stirred for 8 h until TLC indicated completion of the reaction. Water was added and the solution was extracted three times with dichloromethane. The combined organic layers were washed with water and brine, dried over magnesium sulfate, filtered and evaporated. The crude product was purified by flash-chromatography on silica gel with hexane:ethyl acetate (4:2 to 3:2) to give 1.2 g (60%) of the product as a white solid. MS (m/e): 284.4 (M–H$^+$).

Step 2 trans-[4-(2-Oxo-ethyl)-cyclohexyl]-carbamic acid tert-butyl ester

To a solution of trans-(4-tert-butoxycarbonylamino-cyclohexyl)-acetic acid ethyl ester (1.04 g, 4 mmol), in toluene (10 mL) at −78° C. a 1.2 M solution of diisobutylaluminium hydride (DIBAL-H) (5.1 mL, 6 mmol) in toluene was added. The mixture was stirred at −78° C. until TLC after 0.5 h indicated completion of the reaction. Water was added and the solution was extracted three times with dichloromethane. The combined organic layers were washed with water and brine, dried over magnesium sulfate, filtered and evaporated. The crude product was used without purification on the next step. MS (m/e): 242.3 (M+H$^+$).

Intermediate J trans-(4-{2-[4-(4-Fluoro-phenoxy)-piperidin-1-yl]-ethyl}-cyclohexyl)-carbamic acid tert-butyl ester A mixture of 4-(4-fluorophenoxy)piperidine (0.150 g, 0.485 mmol), trans-[4-(2-oxo-ethyl)-cyclohexyl]-carbamic acid tert-butyl ester (0.117 g, 0.48 mmol), in 1, 2 dichloroethane (3 mL) and methanol (0.500 mL) was stirred for 4 hours at room temperature. Sodium triacetoxyborohydride (0.175 g, 0.829 mmol) was added and the resulting solution was stirred for 12 hours until the TLC indicated completion of the reaction. The mixture was filtrated and concentrated to dryness and purified with column chromatography on silica gel using CH$_2$Cl$_2$-CH$_2$Cl$_2$/CH$_3$OH (1-9:1). The product fractions were concentrated to give 0.176 g (0.45 mmol, 92.5% yield) of a light yellow solid. MS (m/e): 393.4 (M+H$^+$).

Intermediate K 1.4 trans-4-{2-[4-(4-Fluoro-Phenoxy)-piperidin-1-yl]-ethyl}-cyclohexylamine trifluoroacetate 0.155 g (0.368 mmol) of trans-(4-{2-[4-(4-fluoro-phenoxy)-piperidin-1-yl]-ethyl}-cyclohexyl)-carbamic acid tert-butyl ester was solved in dichloromethane (2 mL) and trifluoroacetic acid was added at 0° C. (0.230 mL, 3 mmol) and the mixture was stirred at room temperature overnight. NaHCO$_3$ was slowly added until pH 9 and the mixture extracted 3 times with dichloromethane and ethyl acetate. The solvent was evaporated to yield 0.160 g (0.368 mmol, 100%) of a white solid that was used without purification on the next steps. MS (m/e): 321.4 (M+H$^+$).

1.5 1H-Indole-2-carboxylic acid trans-(4-{2-[4-(4-fluoro-phenoxy)-piperidin-1-yl]-ethyl}-cyclohexyl)-amide The title compound was prepared as follows.

1H-Indole-2-carboxylic acid (0.006 g, 0.037 mmol), 2-(1H-benzotriazol-1-yl)-1,1,3,3-tetramethyl uronium tetrafluoroborate (0.011 g, 0.034 mmol) and (0.02 mL, 0.102 mmol) of N-ethyldiisopropylamine were stirred in 0.5 mL of dimethylformamide (DMF) for 0.5 h at room temperature and trans-4-{2-[4-(4-fluoro-phenoxy)-piperidin-1-yl]-ethyl}-cyclohexylamine trifluoro-acetic acid salt (0.015 g, 0.034 mmol) was added. The mixture was stirred for 12 hours at room temperature. The mixture was concentrated to dryness and the residue was taken up on methanol and purified with preparative HPLC on reversed phase eluting with acetonitrile/water. The combined product containing fractions were evaporated under reduced pressure to yield 0.009 g of an off-white solid (0.019 mmol, 52.4%). MS (m/e): 464.2 (M+H$^+$).

Examples 2 to 7

According to the procedure described in Section 1.5 above, further derivatives have been synthesized from the respective trans-4-{2-[4-(4-fluoro-phenoxy)-piperidin-1-yl]-ethyl}-cyclohexylamine and various acids. They comprise examples 2 to 7.

| Ex. No | Systematic name | MW | Starting materials | MW found (M + H)+ |
|---|---|---|---|---|
| 1 | 1H-Indole-2-carboxylic acid trans-(4-{2-[4-(4-fluoro-phenoxy)-piperidin-1-yl]-ethyl}-cyclohexyl)-amide | 463.5 | trans-4-{2-[4-(4-Fluoro-phenoxy)-piperidin-1-yl]-ethyl}-cyclohexylamine and 1H-Indole-2-carboxylic acid | 464.2 |
| 2 | Tetrahydro-pyran-4-carboxylic acid (trans-4-{2-[4-(4-fluoro-phenoxy)-piperidin-1-yl]-ethyl}-cyclohexyl)-amide | 432.6 | trans-4-{2-[4-(4-Fluoro-phenoxy)-piperidin-1-yl]-ethyl}-cyclohexylamine and tetrahydro-pyran-4-carboxylic acid | 433.4 |
| 3 | N-(trans-4-{2-[4-(4-Fluoro-phenoxy)-piperidin-1-yl]-ethyl}-cyclohexyl)-3-methoxy-propionamide | 406.53 | trans-4-{2-[4-(4-Fluoro-phenoxy)-piperidin-1-yl]-ethyl}-cyclohexylamine and 3-methoxy-propionic acid | 407.4 |
| 4 | 4-Chloro-N-trans (4-{2-[4-(4-fluoro-phenoxy)-piperidin-1-yl]-ethyl}-cyclohexyl)-benzamide | 459.0 | trans-4-{2-[4-(4-Fluoro-phenoxy)-piperidin-1-yl]-ethyl}-cyclohexylamine and 4-chloro benzoic acid | 459.4 |
| 5 | N-trans (4-{2-[4-(4-Fluoro-phenoxy)-piperidin-1-yl]-ethyl}-cyclohexyl)-3-(5-methyl-[1,2,4]oxadiazol-3-yl)-benzamide | 506.6 | trans-4-{2-[4-(4-Fluoro-phenoxy)-piperidin-1-yl]-ethyl}-cyclohexylamine and 3-(5-methyl-1,2,4-oxadiazol-3-yl)-benzoic acid | 507.2 |
| 6 | Cyclopropanecarboxylic acid (trans-4-{2-[4-(4-fluoro-phenoxy)-piperidin-1-yl]-ethyl}-cyclohexyl)-amide | 388.5 | trans 4-{2-[4-(4-Fluoro-phenoxy)-piperidin-1-yl]-ethyl}-cyclohexylamine and Cyclopropanecarboxylic acid | 389.3 |
| 7 | N-(4-{2-[4-(4-Fluoro-phenoxy)-piperidin-1-yl]-ethyl}-cyclohexyl)-4-methanesulfonyl-benzamide | 502.6 | Trans 4-{2-[4-(4-Fluoro-phenoxy)-piperidin-1-yl]-ethyl}-cyclohexylamine and 4-methanesulfonyl-benzoic acid | 503.1 |

Example 8

Trans N-(4-{2-[4-(4-Fluoro-phenoxy)-piperidin-1-yl]-ethyl}-cyclohexyl)-acetamide The title compound was prepared as follows.

Trans-4-{2-[4-(4-Fluoro-phenoxy)-piperidin-1-yl]-ethyl}-cyclohexylamine (intermediate K, example 1.4) (0.120 g, 0.276 mmol) was suspended in dichloromethane (2.4 mL) and triethylamine was added (0.964 mL, 0.690 mmol) followed by acetylchloride (0.021 mL, 0.303 mmol) and the mixture was stirred for 2 hours at room temperature until thin layer chromatography (TLC) indicated the end of the reaction. The solvent was removed and dimethylformamide (DMF) (0.8 mL) was added and the solution was purified with preparative HPLC on reversed phase eluting with acetonitrile/water (0.05% Et$_3$N). The combined product fractions were evaporated under reduced pressure to yield 0.016 g of an off-white solid (0.045 mmol, 16.3%). MS (m/e): 363.3 (M+H+)

Example 9

Trans-1-(4-Chloro-phenyl)-3-(4-{2-[4-(4-fluoro-phenoxy)-piperidin-1-yl]-ethyl}-cyclohexyl)-urea The title compound was prepared as follows.

Trans-4-{2-[4-(4-Fluoro-phenoxy)-piperidin-1-yl]-ethyl}-cyclohexylamine, trifluoroacetic acid salt (intermediate K, example 1.4) (0.030 g, 0.07 mmol) was suspended in acetonitrile (0.600 mL) and 4-chlorophenyl isocyanate was added (0.012 g, 0077 mmol) and the mixture was stirred for 2 hours at room temperature until thin layer chromatography (TLC) indicated the end of the reaction. The solvent was removed and the crude was purified with chromatography eluting with dichloromethane/methanol (1/0 to 9/1). The combined product fractions were evaporated under reduced pressure to yield 0.020 g of a white solid (0.042 mmol, 60%). MS (m/e): 474.1 (M+H+)

Example 10

Trans-1-(4-{2-[4-(4-Fluoro-phenoxy)-piperidin-1-yl]-ethyl}-cyclohexyl)-3-p-tolyl-urea According to the procedure described for the synthesis of example 9, 1-Trans(4-{2-[4-(4-Fluoro-phenoxy)-piperidin-1-yl]-ethyl}-cyclohexyl)-3-p-tolyl-urea was synthesized from Trans-{1-[2-(4-Amino-cyclohexyl)-ethyl]-piperidin-4-yl}-(4-fluoro-phenyl)-methanone and p-tolyl isocyanate.

| Ex. No | Systematic name | MW | Starting materials | MW found (M + H)+ |
|---|---|---|---|---|
| 9 | 1-(4-Chloro-phenyl)-3-trans (4-{2-[4-(4-fluoro-phenoxy)-piperidin-1-yl]-ethyl}-cyclohexyl)-urea | 474.02 | Trans-4-{2-[4-(4-Fluoro-phenoxy)-piperidin-1-yl]-ethyl}-cyclohexylamine and 4-chlorophenyl isocyanate | 474.1 |
| 10 | 1-Trans (4-{2-[4-(4-Fluoro-phenoxy)-piperidin-1-yl]-ethyl}-cyclohexyl)-3-p-tolyl-urea | 453.6 | Trans-4-{2-[4-(4-Fluoro-phenoxy)-piperidin-1-yl]-ethyl}-cyclohexylamine and p-tolyl-isocyanate | 454.5 |

Example 11

Quinoline-4-carboxylic acid trans(4-{2[4-(2-chloro-4-fluoro-phenoxy)-piperidin-1-yl]-ethyl}-cyclohexyl)-amide

Intermediate J 11.3 Trans(4-{2-[4-(2-Chloro-4-fluoro-phenoxy)-piperidin-1-yl]-ethyl}-cyclohexyl)-carbamic acid tert-butyl ester According to the synthesis of intermediate J, example 1, the title compound was prepared from 4-(2,3-Dichloro-phenoxy)-piperidine (intermediate D, example 1.2) (0.600 g, 1.7 mmol), Trans-[4-(2-Oxo-ethyl)-cyclohexyl]-carbamic acid tert-butyl ester (0.506 g, 2 mmol) (intermediate H, example 1) and sodium triacetoxyborohydride (0.666 g, 3 mmol) in 1,2-dichloroethane (8 mL). The mixture was filtrated and concentrated to dryness and purified with column chromatography on silica gel using $CH_2Cl_2$-$CH_2Cl_2$/$CH_3OH$ (1-9:1). The product fractions were concentrated to give 0.696 g (1.53 mmol, 87.5% yield) of a light yellow solid. MS (m/e): 467.3 (M+H+).

Intermediate K 11.4 Trans 4-{2-[4-(2-Chloro-4-fluoro-phenoxy)-piperidin-1-yl]-ethyl}-cyclohexylamine; trifluoro-acetic acid salt According to the synthesis of intermediate K, example 1.4, the title compound was prepared from 0.695 g (1.48 mmol) of Trans(4-{2-[4-(2-Chloro-4-fluoro-phenoxy)-piperidin-1-yl]-ethyl}-cyclohexyl)-carbamic acid tert-butyl ester in dichloromethane (8 mL) and trifluoroacetic acid (1.05 mL, 14 mmol) to yield 0.603 g (1.3 mmol, 84.1%) of the title compound as a white solid that was used without purification on the next steps. MS (m/e): 355.3 (M+H+).

11.5 Quinoline-4-carboxylic acid trans(4-{2[4-(2-chloro-4-fluoro-phenoxy)-piperidin-1-yl]-ethyl}-cyclohexyl)-amide The title compound was prepared as follows.

Quinoline-4-carboxylic acid (0.020 g, 0.115 mmol), 2-(1H-benzotriazol-1-yl)-1,1,3,3-tetramethyl uronium tetrafluoroborate (0.035 g, 0.106 mmol) and (0.05 mL, 0.318 mmol) of N-ethyldiisopropylamine were stirred in 0.5 mL of dimethylformamide (DMF) for 0.5 h at room temperature and Trans-4-{2-[4-(4-Fluoro-phenoxy)-piperidin-1-yl]-ethyl}-cyclohexylamine; trifluoro-acetic acid salt (0.050 g, 0.106 mmol) was added. The mixture was stirred for 12 hours at room temperature. The mixture was concentrated to dryness and the residue was taken up on methanol and purified with preparative HPLC on reversed phase eluting with acetonitrile/water. The combined product fractions were evaporated under reduced pressure to yield 0.054 g of a off-white solid (0.101 mmol, 54.9%). MS (m/e): 510.2 (M+H+).

Examples 12 to 18

According to the procedure described for the synthesis of example 11.5, further derivatives have been synthesized from Trans-4-{2-[4-(2-Chloro-4-fluoro-phenoxy)-piperidin-1-yl]-ethyl}-cyclohexylamine; trifluoro-acetic acid salt and various acids. They comprise examples 12 to 18

| Ex. No | Systematic name | MW | Starting materials | MW found (M + H)+ |
|---|---|---|---|---|
| 11 | Quinoline-4-carboxylic acid trans(4-{2[4-(2-chloro-4-fluoro-phenoxy)-piperidin-1-yl]-ethyl}-cyclohexyl)-amide | 510.2 | Trans4-{2-[4-(2-Chloro-4-fluoro-phenoxy)-piperidin-1-yl]-ethyl}-cyclohexylamine and Quinoline-4-carboxylic acid | 510.4 |
| 12 | N-trans(4-{2-[4-(2-Chloro-4-fluoro-phenoxy)-piperidin-1-yl]-ethyl}-cyclohexyl)-4-methanesulfonyl-benzamide | 537.09 | Trans 4-{2-[4-(2-Chloro-4-fluoro-phenoxy)-piperidin-1-yl]-ethyl}-cyclohexylamine and 4-methanesulfonyl-benzoic acid | 538.2 |

-continued

| Ex. No | Systematic name | MW | Starting materials | MW found (M + H)+ |
|---|---|---|---|---|
| 13 | N-trans (4-{2-[4-(2-Chloro-4-fluoro-phenoxy)-piperidin-1-yl]-ethyl}-cyclohexyl)-3-methoxy-propionamide | 440.9 | Trans 4-{2-[4-(2-Chloro-4-fluoro-phenoxy)-piperidin-1-yl]-ethyl}-cyclohexylamine and 3-Methoxy-propionic acid | 441.0 |
| 14 | 4-Chloro-N-trans (4-{2-[4-(2-chloro-4-fluoro-phenoxy)-piperidin-1-yl]-ethyl}-cyclohexyl)-benzamide | 493.45 | Trans 4-{2-[4-(2-Chloro-4-fluoro-phenoxy)-piperidin-1-yl]-ethyl}-cyclohexylamine and 4-Chloro benzoic acid | 493.1 |
| 15 | Tetrahydro-pyran-4-carboxylic acid trans (4-{2-[4-(2-chloro-4-fluoro-phenoxy)-piperidin-1-yl]-ethyl}-cyclohexyl)-amide | 467.02 | Trans 4-{2-[4-(2-Chloro-4-fluoro-phenoxy)-piperidin-1-yl]-ethyl}-cyclohexylamine and Tetrahydro-pyran-4-carboxylic acid | 467.0 |
| 16 | N-trans (4-{2-[4-(2-Chloro-4-fluoro-phenoxy)-piperidin-1-yl]-ethyl}-cyclohexyl)-3-(5-methyl-[1,2,4]oxadiazol-3-yl)-benzamide | 541.06 | Trans 4-{2-[4-(2-Chloro-4-fluoro-phenoxy)-piperidin-1-yl]-ethyl}-cyclohexylamine and 3-(5-methyl-[1,2,4]oxadiazol-3-yl)-benzoic acid | 541.1 |
| 17 | Cyclopropanecarboxylic acid trans (4-{2-[4-(2-chloro-4-fluoro-phenoxy)-piperidin-1-yl]-ethyl}-cyclohexyl)-amide | 422.9 | Trans 4-{2-[4-(2-Chloro-4-fluoro-phenoxy)-piperidin-1-yl]-ethyl}-cyclohexylamine and Cyclopropanecarboxylic acid | 423.3 |
| 18 | N-trans (4-{2-[4-(2-Chloro-4-fluoro-phenoxy)-piperidin-1-yl]-ethyl}-cyclohexyl)-propionamide | 410.9 | Trans 4-{2-[4-(2-Chloro-4-fluoro-phenoxy)-piperidin-1-yl]-ethyl}-cyclohexylamine and propionic acid | 411.0 |

Example 19

N-trans(4-{2-[4-(2-Chloro-4-fluoro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from Trans 4-{2-[4-(2-Chloro-4-fluoro-phenoxy)-piperidin-1-yl]-ethyl}-cyclohexylamine and acetylchloride MS (m/e): 397.0 (M+H+).

Example 20

Trans 1-(4-{2-[4-(2-Chloro-4-fluoro-phenoxy)-piperidin-1-yl]-ethyl}-cyclohexyl)-3-(4-chloro-phenyl)-urea According to the synthesis of Trans 1-(4-Chloro-phenyl)-3-(4-{2-[4-(4-fluoro-phenoxy)-piperidin-1-yl]-ethyl}-cyclohexyl)-urea (example 9) the title compound was prepared from Trans 1-(4-{2-[4-(2-Chloro-4-fluoro-phenoxy)-piperidin-1-yl]-ethyl}-cyclohexylamine and 4-chlorophenyl isocyanate. MS (m/e): 508.3 (M+H+).

Example 21

1-trans(4-{2-[4-(2-Chloro-4-fluoro-phenoxy)-piperidin-1-yl]-ethyl}-cyclohexyl)-3-p-tolyl-urea According to the procedure described for the synthesis of example 20, the title compound was synthesized from Trans-1-(4-{2-[4-(2-Chloro-4-fluoro-phenoxy)-piperidin-1-yl]-ethyl}-cyclohexylamine and p-tolyl-isocyanate.

| Ex. No | Systematic name | MW | Starting materials | MW found (M + H)+ |
|---|---|---|---|---|
| 20 | 1-trans (4-{2-[4-(2-Chloro-4-fluoro-phenoxy)-piperidin-1-yl]-ethyl}-cyclohexyl)-3-(4-chloro-phenyl)-urea | 508.4 | Trans 4-{2-[4-(2-Chloro-4-fluoro-phenoxy)-piperidin-1-yl]-ethyl}-cyclohexylamine and 4-chlorophenyl isocyanate | 508.3 |

-continued

| Ex. No | Systematic name | MW | Starting materials | MW found $(M + H)^+$ |
|---|---|---|---|---|
| 21 | 1-trans (4-{2-[4-(2-Chloro-4-fluoro-phenoxy)-piperidin-1-yl]-ethyl}-cyclohexyl)-3-p-tolyl-urea | 488.05 | Trans-4-{2-[4-(4-Fluoro-phenoxy)-piperidin-1-yl]-ethyl}-cyclohexylamine and p-tolyl-isocyanate | 488.2 |

Example 22

Tetrahydro-pyran-4-carboxylic acid trans(4-{2-[4-(2,4-difluoro-phenoxy)-piperidin-1-yl]-ethyl}-cyclohexyl)-amide Intermediate J 22.3 Trans(4-{2-[4-(2,4-Difluoro-phenoxy)-piperidin-1-yl]-ethyl}-cyclohexyl)-carbamic acid tert-butyl ester According to the synthesis of Trans-(4-{2-[4-(4-Fluoro-phenoxy)-piperidin-1-yl]-ethyl}-cyclohexyl)-carbamic acid tert-butyl ester (intermediate J, example 1.3) the title compound was prepared from (2,4-Difluoro-phenoxy)-piperidine and Trans-[4-(2-Oxo-ethyl)-cyclohexyl]-carbamic acid tert-butyl ester with sodium triacetoxyborohydride in 1,2-dichloroetane. MS (m/e): 439.4 (M+H$^+$).

Intermediate K 22.4 Trans 4-{2-[4-(2,4-Difluoro-phenoxy)-piperidin-1-yl]-ethyl}-cyclohexylamine; compound with trifluoro-acetic acid According to the synthesis of Trans 4-{2-[4-(4-Difluoro-phenoxy)-piperidin-1-yl]-ethyl}-cyclohexylamine (example 1.4) the title compound was prepared from Trans(4-{2-[4-(2,4-Difluoro-phenoxy)-piperidin-1-yl]-ethyl}-cyclohexyl)-carbamic acid tert-butyl ester and trifluoroacetic acid. MS (m/e): 339.3 (M+H$^+$).

22.5 Tetrahydro-pyran-4-carboxylic acid trans(4-{2-[4-(2,4-difluoro-phenoxy)-piperidin-1-yl]-ethyl}-cyclohexyl)-amide According to the synthesis of 1H-Indole-2-carboxylic acid trans-(4-{2-[4-(4-fluoro-phenoxy)-piperidin-1-yl]-ethyl}-cyclohexyl)-amide (example 1) the title compound was prepared from Trans(4-{2-[4-(2,4-Difluoro-phenoxy)-piperidin-1-yl]-ethyl}-cyclohexylamine; trifluoro-acetic acid salt and Tetrahydro-pyran-4-carboxylic acid using 2-(1H-benzotriazol-1-yl)-1,1,3,3-tetramethyl uronium tetrafluoroborate and N-ethyldiisopropylamine in dimethylformamide (DMF). The residue was taken up on methanol and purified with preparative HPLC on reversed phase eluting with acetonitrile/water. MS (m/e): 451.3. (M+H$^+$).

Example 23

Quinoline-6-carboxylic acid trans(4-{2-[4-(2,4-difluoro-phenoxy)-piperidin-1-yl]-ethyl}-cyclohexyl)-amide According to the procedure described in Example 22.5, the title compound was synthesized from Trans(4-{2-[4-(2,4-Difluoro-phenoxy)-piperidin-1-yl]-ethyl}-cyclohexylamine; trifluoro-acetic acid salt and quinoline-6-carboxylic acid.

Example 24

Quinoline-4-carboxylic acid trans(4-{2-[4-(2,4-difluoro-phenoxy)-piperidin-1-yl]-ethyl}-cyclohexyl)-amide According to the procedure described in Example 22.5, the title compound was synthesized from Trans(4-{2-[4-(2,4-Difluoro-phenoxy)-piperidin-1-yl]-ethyl}-cyclohexylamine; trifluoro-acetic acid salt and quinoline-4-carboxylic acid.

| Ex. No | Systematic name | MW | Starting materials | MW found $(M + H)^+$ |
|---|---|---|---|---|
| 22 | Tetrahydro-pyran-4-carboxylic acid trans (4-{2-[4-(2,4-difluoro-phenoxy)-piperidin-1-yl]-ethyl}-cyclohexyl)-amide | 450.5 | Trans (4-{2-[4-(2,4-Difluoro-phenoxy)-piperidin-1-yl]-ethyl}-cyclohexylamine; trifluoroacetic acid salt and Tetrahydro-pyran-4-carboxylic acid | 451.3 |
| 23 | Quinoline-6-carboxylic acid trans (4-{2-[4-(2,4-difluoro-phenoxy)-piperidin-1-yl]-ethyl}-cyclohexyl)-amide | 493.6 | Trans (4-{2-[4-(2,4-Difluoro-phenoxy)-piperidin-1-yl]-ethyl}-cyclohexylamine; trifluoroacetic acid salt and Quinoline-6-carboxylic acid | 494.5 |
| 24 | Quinoline-4-carboxylic acid trans (4-{2-[4-(2,4-difluoro-phenoxy)-piperidin-1-yl]-ethyl}-cyclohexyl)-amide | 493.5 | Trans (4-{2-[4-(2,4-Difluoro-phenoxy)-piperidin-1-yl]-ethyl}-cyclohexylamine; trifluoroacetic acid salt and Quinoline-4-carboxylic acid | 494.4 |

Example 25

N-Trans(4-{2-[4-(2,4-Difluoro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from Trans(4-{2-[4-(2,4-Difluoro-phenoxy)-piperidin-1-yl]-ethyl}-cyclohexylamine; trifluoroacetic acid salt and acetylchloride MS (m/e): 381.3 (M+H$^+$).

Example 26

Cyclobutanecarboxylic acid trans(4-{2-[4-(2-cyano-4-fluoro-phenoxy)-piperidin-1-yl]-ethyl}-cyclohexyl)-amide Intermediate C 26.1 4-(2-Cyano-4-fluoro-phenoxy)-piperidine-1-carboxylic acid tert-butyl ester The title compound was prepared a follows.
2-5-Difluorobenzonitrile (1.00 g, 7.2 mmol) was added at room temperature to a stirred mixture under argon of sodium hydride (55%, 207 mg, 9 mmol) in dimethylformamide (DMF) (10 ml). 4-Hydroxypiperidine-1-carboxylic acid tert-butyl ester (3.32 g, 17 mmol) was added in portions. The resulting mixture was stirred several hours at 50° C. before partitioning it between H$_2$O and ethyl acetate (EtOAc). The organic layer was washed with sat. aq. NH$_4$Cl sol. and brine and dried over MgSO$_4$. Evaporation of the solvent yielded 2.24 g (97.2%, 7 mmol) of a light brown solid. MS (m/z): 321.1 (M+H$^+$).

Intermediate D 26.2 5-Fluoro-2-(piperidin-4-yloxy)-benzonitrile; hydrochloride

The title compound was prepared as follows.

A solution 4-(2-Cyano-4-fluoro-phenoxy)-piperidine-1-carboxylic acid tert-butyl ester (2.2 g, 0.7 mmol) in CH$_2$Cl$_2$ (20 ml) was treated with sat. HCl sol. in diethyl ether (Et$_2$O) (10 ml). After 3 hours, the formed solid was collected by filtration and washed with Et$_2$O to yield 1.7 g (95%, 0.68 mmol) of a light brown solid. MS (m/z): 221.3 (M+H$^+$)

26.3 Trans(4-{2-[4-(2-Cyano-4-fluoro-phenoxy)-piperidin-1-yl]-ethyl}-cyclohexyl)-carbamic acid tert-butyl ester The title compound was prepared analogously to example 1 (1.3) starting from 5-Fluoro-2-(piperidin-4-yloxy)-benzonitrile; hydrochloride and Trans-[4-(2-Oxo-ethyl)-cyclohexyl]-carbamic acid tert-butyl ester with sodium triacetoxyborohydride in 1,2-dichloroetane. MS (m/e): 446.3 (M+H$^+$)

26.4 Trans 2-{1-[2-(4-Amino-cyclohexyl)-ethyl]-piperidin-4-yloxy}-5-fluoro-benzonitrile; compound with trifluoro-acetic acid The title compound was prepared analogously to example 1 (1.4) starting from Trans(4-{2-[4-(2-Cyano-4-fluoro-phenoxy)-piperidin-1-yl]-ethyl}-cyclohexyl)-carbamic acid tert-butyl ester and trifluoroacetic acid MS (m/e): 346.2 (M+H$^+$).

26.5 Cyclobutanecarboxylic acid (4-{2-[4-(2-cyano-4-fluoro-phenoxy)-piperidin-1-yl]-ethyl}-cyclohexyl)-amide The title compound was prepared analogously to example 1 (1.5) from Trans 2-{1-[2-(4-Amino-cyclohexyl)-ethyl]-piperidin-4-yloxy}-5-fluoro-benzonitrile; trifluoro-acetic acid salt and cyclobutanecarboxylic acid using 2-(1H-benzotriazol-1-yl)-1,1,3,3-tetramethyl uronium tetrafluoroborate and N-ethyldiisopropylamine in dimethylformamide (DMF). The residue was taken up on methanol and purified with preparative HPLC on reversed phase eluting with acetonitrile/water. MS (m/e): 428.0. (M+H$^+$).

Examples 27 to 33

Using the procedure described in example 26.5, further derivatives have been synthesized from Trans 2-{1-[2-(4-Amino-cyclohexyl)-ethyl]-piperidin-4-yloxy}-5-fluoro-benzonitrile and various acids. They comprise examples 27 to 33.

| Ex. No | Systematic name | MW | Starting materials | MW found (M + H)$^+$ |
|---|---|---|---|---|
| 26 | Cyclobutanecarboxylic acid trans (4-{2-[4-(2-cyano-4-fluoro-phenoxy)-piperidin-1-yl]-ethyl}-cyclohexyl)-amide | 427.5 | Trans 2-{1-[2-(4-Amino-cyclohexyl)-ethyl]-piperidin-4-yloxy}-5-fluoro-benzonitrile and Cyclobutanecarboxylic acid | 428.0 |
| 27 | Tetrahydro-pyran-4-carboxylic acid trans (4-{2-[4-(2-cyano-4-fluoro-phenoxy)-piperidin-1-yl]-ethyl}-cyclohexyl)-amide | 457.5 | Trans 2-{1-[2-(4-Amino-cyclohexyl)-ethyl]-piperidin-4-yloxy}-5-fluoro-benzonitrile and Tetrahydro-pyran-4-carboxylic acid | 458.3 |
| 28 | 4-Chloro-N-trans (4-{2-[4-(2-cyano-4-fluoro-phenoxy)-piperidin-1-yl]-ethyl}-cyclohexyl)-benzamide | 484.0 | Trans 2-{1-[2-(4-Amino-cyclohexyl)-ethyl]-piperidin-4-yloxy}-5-fluoro-benzonitrile and 4-Chloro benzoic acid | 484.3 |
| 29 | N-Trans (4-{2-[4-(2-Cyano-4-fluoro-phenoxy)-piperidin-1-yl]-ethyl}-cyclohexyl)-4-methoxy-benzamide | 479.6 | Trans 2-{1-[2-(4-Amino-cyclohexyl)-ethyl]-piperidin-4-yloxy}-5-fluoro-benzonitrile and 4-Methoxy-benzoic acid | 480.3 |
| 30 | N-Trans (4-{2-[4-(2-Cyano-4-fluoro-phenoxy)-piperidin-1-yl]-ethyl}-cyclohexyl)-3-methoxy-propionamide | 413.5 | Trans 2-{1-[2-(4-Amino-cyclohexyl)-ethyl]-piperidin-4-yloxy}-5-fluoro-benzonitrile and 3-Methoxy-propionic acid | 414.3 |
| 31 | Cyclopropanecarboxylic acid trans (4-{2-[4-(2-cyano-4-fluoro-phenoxy)-piperidin-1-yl]-ethyl}-cyclohexyl)-amide | 431.5 | Trans 2-{1-[2-(4-Amino-cyclohexyl)-ethyl]-piperidin-4-yloxy}-5-fluoro-benzonitrile and Cyclopropanecarboxylic acid | 432.2 |
| 32 | 2-Methyl-cyclopropanecarboxylic acid trans (4-{2-[4-(2-cyano-4-fluoro-phenoxy)-piperidin-1-yl]-ethyl}-cyclohexyl)-amide | 427.5 | Trans 2-{1-[2-(4-Amino-cyclohexyl)-ethyl]-piperidin-4-yloxy}-5-fluoro-benzonitrile and 2-Methyl-cyclopropanecarboxylic | 428.4 |
| 33 | Thiophene-2-carboxylic acid trans (4-{2-[4-(2-cyano-4-fluoro-phenoxy)-piperidin-1-yl]-ethyl}-cyclohexyl)-amide | 455.6 | Trans 2-{1-[2-(4-Amino-cyclohexyl)-ethyl]-piperidin-4-yloxy}-5-fluoro-benzonitrile and Thiophene-2-carboxylic acid | 456.3 |

Example 34

Trans N-(4-{2-[4-(2-Cyano-4-fluoro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from Trans 2-{1-

[2-(4-Amino-cyclohexyl)-ethyl]-piperidin-4-yloxy}-5-fluoro-benzonitrile; trifluoroacetic acid salt and acetylchloride MS (m/e): 381.3 (M+H$^+$).

Example 35

Trans N-(4-{2-[4-(2-Cyano-4-fluoro-phenoxy)-piperidin-1-yl]-ethyl}-cyclohexyl)-2,2,2-trifluoro-acetamide The title compound was obtained as a by-product from the reaction of Trans(4-{2-[4-(2-cyano-4-fluoro-phenoxy)-piperidin-1-yl]-ethyl}-cyclohexyl)-amine; trifluoroacetic acid salt and acetylchloride (example 34) MS (m/e): 442.3 (M+H$^+$).

Example 36

Cyclobutanecarboxylic acid trans(4-{2-[4-(2,3-dichloro-phenoxy)-piperidin-1-yl]-ethyl}-cyclohexyl)-amide According to the synthesis of 1H-Indole-2-carboxylic acid trans-(4-{2-[4-(4-fluoro-phenoxy)-piperidin-1-yl]-ethyl}-cyclohexyl)-amide (example 1) the title compound was prepared from Trans(4-{2-[4-(2,3-dichloro-phenoxy)-piperidin-1-yl]-ethyl}-cyclohexyl)-amine and Cyclobutanecarboxylic acid using 2-(1H-benzotriazol-1-yl)-1,1,3,3-tetramethyl uronium tetrafluoroborate and N-ethyldiisopropylamine in dimethylformamide (DMF). The residue was taken up on methanol and purified with preparative HPLC on reversed phase eluting with acetonitrile/water. MS (m/e): 453.0. (M+H$^+$).

Examples 37 to 39

Using the same procedure as in Example 36, further derivatives have been synthesized from Trans(4-{2-[4-(2,3-dichloro-phenoxy)-piperidin-1-yl]-ethyl}-cyclohexyl)-amine and various acids. They comprise examples 37 to 39.

| Ex. No | Systematic name | MW | Starting materials | MW found (M + H)$^+$ |
|---|---|---|---|---|
| 36 | Cyclobutanecarboxylic acid trans (4-{2-[4-(2,3-dichloro-phenoxy)-piperidin-1-yl]-ethyl}-cyclohexyl)-amide | 453.4 | Trans (4-{2-[4-(2,3-dichloro-phenoxy)-piperidin-1-yl]-ethyl}-cyclohexyl)-amine and Cyclobutanecarboxylic acid | 453.0 |
| 37 | Trans N-(4-{2-[4-(2,3-Dichloro-phenoxy)-piperidin-1-yl]-ethyl}-cyclohexyl)-3-methoxy-propionamide | 457.4 | Trans (4-{2-[4-(2,3-dichloro-phenoxy)-piperidin-1-yl]-ethyl}-cyclohexyl)-amine and 3-methoxy-propionic acid | 457.2 |
| 38 | Thiophene-2-carboxylic acid trans (4-{2-[4-(2,3-dichloro-phenoxy)-piperidin-1-yl]-ethyl}-cyclohexyl)-amide | 481.4 | Trans (4-{2-[4-(2,3-dichloro-phenoxy)-piperidin-1-yl]-ethyl}-cyclohexyl)-amine and Thiophene-2-carboxylic acid | 481.1 |
| 39 | Tetrahydro-pyran-4-carboxylic acid trans (4-{2-[4-(2,3-dichloro-phenoxy)-piperidin-1-yl]-ethyl}-cyclohexyl)-amide | 483.4 | Trans (4-{2-[4-(2,3-dichloro-phenoxy)-piperidin-1-yl]-ethyl}-cyclohexyl)-amine and Tetrahydro-pyran-4-carboxylic acid | 483.3 |

Example 40

N-Trans(4-{2-[4-(2,3-Dichloro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from the reaction of Trans(4-{2-[4-(2,3-dichloro-phenoxy)-piperidin-1-yl]-ethyl}-cyclohexyl)-amine and acetylchloride. MS (m/e): 415.3 (M+H$^+$).

Example 41

Cyclobutanecarboxylic acid trans(4-{2-[4-(2,6-dichloro-4-fluoro-phenoxy)-piperidin-1-yl]-ethyl}-cyclohexyl)-amide According to the synthesis of example 1 the title compound was prepared from Trans(4-{2-[4-(2,6-dichloro-4-fluoro-phenoxy)-piperidin-1-yl]-ethyl}-cyclohexyl)-amine and cyclobutanecarboxylic acid. Preparative HPLC on reversed phase eluting with acetonitrile/water yielded the title compound. MS (m/e): 471.0 (M+H$^+$).

Examples 42 to 45

Using the same procedure as in example 45 further derivatives have been synthesized from Trans(4-{2-[4-(2,6-dichloro-4-fluoro-phenoxy)-piperidin-1-yl]-ethyl}-cyclohexyl)-amine and various acids. They comprise examples 42 to 45.

| Ex. No | Systematic name | MW | Starting materials | MW found (M + H)$^+$ |
|---|---|---|---|---|
| 41 | Cyclobutanecarboxylic acid trans (4-{2-[4-(2,3-dichloro-phenoxy)-piperidin-1-yl]-ethyl}-cyclohexyl)-amide | 471.4 | Trans (4-{2-[4-(2,6-dichloro-4-fluoro-phenoxy)-piperidin-1-yl]-ethyl}-cyclohexyl)-amine and Cyclobutanecarboxylic acid. | 471.0 |
| 42 | Tetrahydro-furan-2-carboxylic acid trans (4-{2-[4-(2,6-dichloro-4-fluoro-phenoxy)-piperidin-1-yl]-ethyl}-cyclohexyl)-amide | 487.4 | Trans (4-{2-[4-(2,6-dichloro-4-fluoro-phenoxy)-piperidin-1-yl]-ethyl}-cyclohexyl)-amine and Tetrahydro-furan-2-carboxylic acid | 487.2 |
| 43 | Tetrahydro-pyran-4-carboxylic acid trans (4-{2-[4-(2,6-dichloro-4-fluoro-phenoxy)-piperidin-1-yl]-ethyl}-cyclohexyl)-amide | 501.4 | Trans (4-{2-[4-(2,6-dichloro-4-fluoro-phenoxy)-piperidin-1-yl]-ethyl}-cyclohexyl)-amine and Tetrahydro-pyran-4-carboxylic acid | 501.4 |
| 44 | N-trans (4-{2-[4-(2,6-Dichloro-4-fluoro-phenoxy)-piperidin-1-yl]-ethyl}-cyclohexyl)-3-methoxy-propionamide | 475.4 | Trans (4-{2-[4-(2,6-dichloro-4-fluoro-phenoxy)-piperidin-1-yl]-ethyl}-cyclohexyl)-amine and 3-methoxy-propionic acid | 475.1 |
| 45 | Thiophene-2-carboxylic acid trans (4-{2-[4-(2,6-dichloro-4-fluoro-phenoxy)-piperidin-1-yl]-ethyl}-cyclohexyl)-amide | 499.4 | Trans (4-{2-[4-(2,6-dichloro-4-fluoro-phenoxy)-piperidin-1-yl]-ethyl}-cyclohexyl)-amine and Thiophene-2-carboxylic acid | 499.4 |

Example 46

N-Trans(4-{2-[4-(2,6-Dichloro-4-fluoro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from Trans(4-{2-[4-(2,6-dichloro-4-fluoro-phenoxy)-piperidin-1-yl]-ethyl}-cyclohexyl)-amine and acetylchloride. MS (m/e): 432.3 (M+H$^+$).

Example 47

Cyclobutanecarboxylic acid trans(4-{2-[4-(2,4,6-trifluoro-phenoxy)-piperidin-1-yl]-ethyl}-cyclohexyl)-amide According to the synthesis of example 19 the title compound was prepared from Trans(4-{2-[4-(2,4,6-trifluoro-phenoxy)-piperidin-1-yl]-ethyl}-cyclohexyl)-amine and Cyclobutanecarboxylic acid. Preparative HPLC on reversed phase eluting with acetonitrile/water yielded the title compound. MS (m/e): 439.0 (M+H$^+$).

Examples 48 to 50

Using the same procedure as in Example 47, further derivatives have been synthesized from. Trans(4-{2-[4-(2,4,6-trifluoro-phenoxy)-piperidin-1-yl]-ethyl}-cyclohexyl)-amine and various acids. They comprise examples 48 to 50.

| Ex. No | Systematic name | MW | Starting materials | MW found (M + H)$^+$ |
|---|---|---|---|---|
| 47 | Cyclobutanecarboxylic acid trans (4-{2-[4-(2,3-dichloro-phenoxy)-piperidin-1-yl]-ethyl}-cyclohexyl)-amide | 438.5 | Trans (4-{2-[4-(2,4,6-trifluoro-phenoxy)-piperidin-1-yl]-ethyl}-cyclohexyl)-amine and Cyclobutanecarboxylic acid | 439.0 |
| 48 | Tetrahydro-furan-2-carboxylic acid trans (4-{2-[4-(2,4,6-trifluoro-phenoxy)-piperidin-1-yl]-ethyl}-cyclohexyl)-amide | 454.5 | Trans (4-{2-[4-(2,4,6-trifluoro-phenoxy)-piperidin-1-yl]-ethyl}-cyclohexyl)-amine and Tetrahydro-furan-2-carboxylic acid | 455.4 |
| 49 | 4-Methoxy-N-trans (4-{2-[4-(2,4,6-trifluoro-phenoxy)-piperidin-1-yl]-ethyl}-cyclohexyl)-benzamide | 490.5 | Trans (4-{2-[4-(2,4,6-trifluoro-phenoxy)-piperidin-1-yl]-ethyl}-cyclohexyl)-amine and 4-Methoxy benzoic acid | 491.2 |
| 50 | 4-Chloro-N-trans (4-{2-[4-(2,4,6-trifluoro-phenoxy)-piperidin-1-yl]-ethyl}-cyclohexyl)-benzamide | 494.9 | Trans (4-{2-[4-(2,4,6-trifluoro-phenoxy)-piperidin-1-yl]-ethyl}-cyclohexyl)-amine and 4-Chloro benzoic acid | 495.2 |

Example 51

Tetrahydro-pyran-4-carboxylic acid trans(4-{2-[4-(2,4,5-trifluoro-phenoxy)-piperidin-1-yl]-ethyl}-cyclohexyl)-amide According to the synthesis of example 19 the title compound was prepared from Trans(4-{2-[4-(2,4,5-trifluoro-phenoxy)-piperidin-1-yl]-ethyl}-cyclohexyl)-amine and tetrahydro-pyran-4-carboxylic acid. Preparative HPLC on reversed phase eluting with acetonitrile/water yielded the title compound. MS (m/e): 469.5 (M+H$^+$).

Examples 52 to 56

Using the same procedure as in example 51, further derivatives have been synthesized using Trans(4-{2-[4-(2,4,5-trifluoro-phenoxy)-piperidin-1-yl]-ethyl}-cyclohexyl)-amine and various acids. They comprise examples 52 to 56.

| Ex. No | Systematic name | MW | Starting materials | MW found (M + H)$^+$ |
|---|---|---|---|---|
| 51 | Tetrahydro-pyran-4-carboxylic acid trans (4-{2-[4-(2,4,5-trifluoro-phenoxy)-piperidin-1-yl]-ethyl}-cyclohexyl)-amide | 468.5 | Trans (4-{2-[4-(2,4,5-trifluoro-phenoxy)-piperidin-1-yl]-ethyl}-cyclohexyl)-amine and Tetrahydro-pyran-4-carboxylic acid | 469.5 |
| 52 | Cyclobutanecarboxylic acid trans (4-{2-[4-(2,4,5-trifluoro-phenoxy)-piperidin-1-yl]-ethyl}-cyclohexyl)-amide | 438.5 | Trans (4-{2-[4-(2,4,5-trifluoro-phenoxy)-piperidin-1-yl]-ethyl}-cyclohexyl)-amine and Cyclobutanecarboxylic acid | 439.0 |
| 53 | 2-Methyl-cyclopropanecarboxylic acid trans (4-{2-[4-(2,4,5-trifluoro-phenoxy)-piperidin-1-yl]-ethyl}-cyclohexyl)-amide | 438.5 | Trans (4-{2-[4-(2,4,5-trifluoro-phenoxy)-piperidin-1-yl]-ethyl}-cyclohexyl)-amine and 2-Methyl-cyclopropanecarboxylic acid | 439.5 |
| 54 | 4-Methoxy-N-trans (4-{2-[4-(2,4,5-trifluoro-phenoxy)-piperidin-1-yl]-ethyl}-cyclohexyl)-benzamide | 490.5 | Trans (4-{2-[4-(2,4,5-trifluoro-phenoxy)-piperidin-1-yl]-ethyl}-cyclohexyl)-amine and 4-Methoxy benzoic acid | 491.2 |
| 55 | 4-Chloro-N-trans (4-{2-[4-(2,4,5-trifluoro-phenoxy)-piperidin-1-yl]-ethyl}-cyclohexyl)-benzamide | 494.9 | Trans (4-{2-[4-(2,4,5-trifluoro-phenoxy)-piperidin-1-yl]-ethyl}-cyclohexyl)-amine and 4-Chloro benzoic acid | 495.2 |
| 56 | Thiophene-2-carboxylic acid trans (4-{2-[4-(2,4,5-trifluoro-phenoxy)-piperidin-1-yl]-ethyl}-cyclohexyl)-amide | 466.5 | Trans (4-{2-[4-(2,4,5-trifluoro-phenoxy)-piperidin-1-yl]-ethyl}-cyclohexyl)-amine and Thiophene-2-carboxylic acid | 467.2 |

Example 57

N-trans(4-{2-[4-(2,4,5-Trifluoro-phenoxy)-piperidin-1-yl]-ethyl}-cyclohexyl)-acetamide According to the synthesis of N-Trans(4-{2-[4-(4-Fluoro-phenoxy)-piperidin-1-yl]-ethyl}-cyclohexyl)-acetamide (example 8), the title compound was prepared from Trans(4-{2-[4-(2,4,5-trifluoro-phenoxy)-piperidin-1-yl]-ethyl}-cyclohexyl)-amine and acetylchloride. MS (m/e): 399.3 (M+H$^+$).

Example 58

Thiophene-2-carboxylic acid trans(4-{2-[4-(4-cyano-2-fluoro-Phenoxy)-piperidin-1-yl]-ethyl}-cyclohexyl)-amide According to the synthesis of example 1, the title compound was prepared from Trans 4-{1-[2-(4-Amino-cyclohexyl)-ethyl]-piperidin-4-yloxy}-3-fluoro-benzonitrile and Thiophene-2-carboxylic acid. Preparative HPLC on reversed phase eluting with acetonitrile/water yielded the title compound. MS (m/e): 456.3 (M+H$^+$).

Example 59

N-trans(4-{2-[4-(2-Cyano-phenoxy)-piperidin-1-yl]-ethyl}-cyclohexyl)-acetamide

59.1 4-(2-Cyano-phenoxy)-piperidine-1-carboxylic acid tert-butyl ester

The title compound was prepared as follows.
2-Fluorobenzonitrile (2.00 g, 17 mmol) was added at room temperature to a stirred mixture under argon of NaH (60%, 793 mg, 20 mmol) in dimethylformamide (DMF) (20 ml). 4-Hydroxypiperidine-1-carboxylic acid tert-butyl ester (3.32 g, 17 mmol) was added in portions. The resulting mixture was stirred several hours at 50° C. before partitioning it between H$_2$O and ethyl acetate (EtOAc). The organic layer was washed with sat. aq. NH$_4$Cl sol. and brine and dried over MgSO$_4$. Evaporation of the solvent yielded 5.65 g (quant., 0.17 mmol) of a yellow oil. MS (m/z): 303.1 (M+H$^+$).

59.2 2-(Piperidin-4-yloxy)-benzonitrile hydrochloride

The title compound was prepared as follows.
A solution of 4-(2-cyano-phenoxy)-piperidine-1-carboxylic acid tert-butyl ester (5.14 g, 17 mmol) in CH$_2$Cl$_2$ (40 ml) was treated with sat. HCl sol. in diethyl ether (Et$_2$O) (20 ml). After 2 hours the formed solid was collected by filtration and washed with Et$_2$O to yield 3.38 g (83%, 14 mmol) of a white powder. MS (m/z): 202.2 (M++).

59.3 Trans-4-{2-[4-(2-Cyano-phenoxy)-piperidin-1-yl]-ethyl}-cyclohexyl)-carbamic acid tert-butyl ester The title compound was prepared as follows.
A solution of 2-(piperidin-4-yloxy)-benzonitrile hydrochloride (255 mg, 1.07 mmol) and [trans-4-(2-oxo-ethyl)-cyclohexyl]-carbamic acid tert-butyl ester (284 mg, 1.18 mmol) in 1,2-dichloroethane (5 ml) was stirred over night at room temperature. Sodium triacetoxyborohydride (Na(AcO)$_3$BH) (340 mg, 1.60 mmol) was added and stirring continued for 24 hours. The mixture was partitioned between H$_2$O and EtOAc. The organic layer was washed with sat. aq. NaHCO$_3$ sol. and brine. After drying (MgSO$_4$) the solvent was evaporated and the product was purified by chromatography (CH$_2$Cl$_2$ to CH$_2$Cl$_2$/CH$_3$OH 9:1) to yield 315 mg (69%, 0.74 mmol) of an off-white solid. MS (m/z): 428.4 (M+H$^+$).

59.4 2-{1-[2-(trans-4-Amino-cyclohexyl)-ethyl]-piperidin-4-yloxy}-benzonitrile hydrochloride The title compound was prepared as follows.
A solution of Trans-4-{2-[4-(2-cyano-phenoxy)-piperidin-1-yl]-ethyl}-cyclohexyl)-carbamic acid tert-butyl ester (305 mg, 0.71 mmol) in CH$_2$Cl$_2$ (3 ml) was treated with sat. HCl sol. in Et$_2$O (2 ml). After 2 hours the formed solid was collected by filtration and washed with Et$_2$O to yield 249 mg (96%, 0.68 mmol) of a white powder. MS (m/z): 328.2 (M+H$^+$)

59.5 N-(trans-4-{2-[4-(2-Cyano-phenoxy)-piperidin-1-yl]-ethyl}-cyclohexyl)-acetamide The title compound was prepared as follows.
To a solution of acetic acid (AcOH) (21 mg, 0.34 mmol) in DMF (3 ml) were subsequently added tetramethyluronium tetrafluoroborate (TBTU) (111 mg, 0.34 mmol) and triethylamine (Et$_3$N) (100 mg, 0.98 mmol). After stirring for 90 minutes at room temperature 2-{1-[2-(trans-4-amino-cyclohexyl)-ethyl]-piperidin-4-yloxy}-benzonitrile hydrochloride (120 mg, 0.33 mmol) was added. Stirring was continued over night, then the solvent was evaporated and the residue partitioned between H$_2$O and EtOAc. The organic layer was washed with sat. aq. NaHCO$_3$ sol. and brine and dried over MgSO$_4$. Solvent evaporation afforded 102 mg (84%, 0.28 mmol) of an off-white solid. MS (m/z): 370.2 (M+H$^+$).

Examples 60 and 61

Using the procedure of example 59, further derivatives have been synthesized using 2-{1-[2-(trans-4-amino-cyclohexyl)-ethyl]-piperidin-4-yloxy}-benzonitrile hydrochloride and various acids. They comprise examples 60 and 61.

| Ex. No | Systematic name | MW | Starting materials | MW found (M + H)$^+$ |
|---|---|---|---|---|
| 59 | N-(trans-4-{2-[4-(2-Cyano-phenoxy)-piperidin-1-yl]-ethyl}-cyclohexyl)-acetamide | 369.5 | 2-{1-[2-(trans-4-amino-cyclohexyl)-ethyl]-piperidin-4-yloxy}-benzonitrile hydrochloride and acetic acid | 370.2 |
| 60 | Quinoline-4-carboxylic acid (trans-4-{2-[4-(2-cyano-phenoxy)-piperidin-1-yl]-ethyl}-cyclohexyl)-amide | 482.6 | 2-{1-[2-(trans-4-amino-cyclohexyl)-ethyl]-piperidin-4-yloxy}-benzonitrile hydrochloride and quinoline-4-carboxylic acid | 483.3 |
| 61 | N-(trans-4-{2-[4-(2-Cyano-phenoxy)-piperidin-1-yl]-ethyl}-cyclohexyl)-4-ethoxy-benzamide | 475.63 | 2-{1-[2-(trans-4-amino-cyclohexyl)-ethyl]-piperidin-4-yloxy}-benzonitrile hydrochloride and 4-ethoxy-benzoic acid | 476.1 |

Example 62

N-trans-(4-{2-[4-(4-Chloro-2-cyano-Phenoxy)-piperidin-1-yl]-ethyl}-cyclohexyl)-acetamide

62.1 2-{1-[2-(trans-4-Amino-cyclohexyl)-ethyl]-piperidin-4-yloxy}-5-chloro-benzonitrile hydrochloride The title compound was prepared analogously to example 59.4 starting from 5-chloro-2-fluorobenzonitrile. MS (m/z): 362.3 (M+H$^+$).

62.1 N-(trans-4-{2-[4-(4-Chloro-2-cyano-phenoxy)-piperidin-1-yl]-ethyl}-cyclohexyl)-acetamide The title compound was prepared analogously to example 59.5 from 2-{1-[2-(trans-4-amino-cyclohexyl)-ethyl]-piperidin-4-yloxy}-5-chloro-benzonitrile hydrochloride and acetic acid. MS (m/z): 404.5 (M+H$^+$).

Examples 63 and 64

Using the procedure of example 62, further derivatives have been synthesized using 2-{1-[2-(trans-4-amino-cyclohexyl)-ethyl]-piperidin-4-yloxy}-5-chloro-benzonitrile hydrochloride and various acids. They comprise examples 63 to 64.

| Ex. No | Systematic name | MW | Starting materials | MW found (M + H)$^+$ |
|---|---|---|---|---|
| 62 | N-(trans-4-{2-[4-(4-Chloro-2-cyano-phenoxy)-piperidin-1-yl]-ethyl}-cyclohexyl)-acetamide | | 2-{1-[2-(trans-4-amino-cyclohexyl)-ethyl]-piperidin-4-yloxy}-5-chloro-benzonitrile hydrochloride and acetic acid | 404.5 |
| 63 | Cyclopropane-carboxylic acid trans (4-{2-[4-(4-chloro-2-cyano-phenoxy)-piperidin-1-yl]-ethyl}-cyclohexyl)-amide | | 2-{1-[2-(trans-4-amino-cyclohexyl)-ethyl]-piperidin-4-yloxy}-5-chloro-benzonitrile hydrochloride and Cyclopropanecarboxylic acid | 430.5 |
| 64 | Tetrahydro-pyran-4-carboxylic acid trans (4-{2-[4-(4-chloro-2-cyano-phenoxy)-piperidin-1-yl]-ethyl}-cyclohexyl)-amide | | 2-{1-[2-(trans-4-amino-cyclohexyl)-ethyl]-piperidin-4-yloxy}-5-chloro-benzonitrile hydrochloride and Tetrahydro-pyran-4-carboxylic acid | 474.3 |

Example 65

N-trans 4-{2-[4-(3-Chloro-2-cyano-phenoxy)-piperidin-1-yl]-ethyl}-cyclohexyl)-acetamide

Intermediate O (trans-4-Acetylamino-cyclohexyl)-acetic acid ethyl ester

The title compound was prepared as follows.
(trans-4-Amino-cyclohexyl)-acetic acid ethyl ester (10.0 g, 45 mmol) was dissolved in CH$_2$Cl$_2$ (150 ml) and Et$_3$N and acetyl chloride (3.89 g, 50 mmol) were added. The reaction mixture was stirred for 3 hours at room temperature before washing with H$_2$O and brine. After drying (Na$_2$SO$_4$) the solvent was evaporated to yield 8.42 g (82%, 37 mmol) of a white solid. MS (m/z): 228.3 ([M+H]$^+$).

Intermediate P

N-[trans-4-(2-Hydroxy-ethyl)-cyclohexyl]-acetamide

The title compound was prepared as follows.
LiAlH$_4$ (2.10 g, 55 mmol) and tetrahydrofuran (THF) (150 ml) were placed in a dry balloon. After cooling this mixture to 0° C., a solution of (trans-4-acetylamino-cyclohexyl)-acetic acid ethyl ester (8.42 g, 37 mmol) in little THF was added dropwise. The reaction was stirred for 1 hour before careful neutralization with H$_2$O (5.6 ml), 1 N NaOH (3×5.6 ml) and more H$_2$O (5.6 ml). The resulting mixture was stirred over night before filtering off the solids. Evaporation of the solvent and drying under high vacuum afforded 5.25 g (76%, 28 mmol) of a light brown solid. MS (m/z): 186.4 ([M+H$^+$]).

Intermediate Q

N-[trans-4-(2-Oxo-ethyl)-cyclohexyl]-acetamide

The title compound was prepared as follows.
Dimethyl sulfoxide (DMSO) (3.68 g, 47 mmol) in CH$_2$Cl$_2$ (20 ml) was added at −78° C. to a stirred solution of oxalyl-chloride (2.9 g, 23 mmol) in CH$_2$Cl$_2$ (100 ml). After 1 hour stirring at −78° C. a solution of N-[trans-4-(2-hydroxy-ethyl)-cyclohexyl]-acetamide (2.18 g, 12 mmol) in CH$_2$Cl$_2$ (80 ml) was added followed after 2 hours by triethylamine (Et$_3$N) (7.14 g, 71 mmol). The mixture was allowed to reach room temperature and was then diluted with H$_2$O and extracted with CH$_2$Cl$_2$. The combined organic layers were dried (Na$_2$SO$_4$) and the solvent was evaporated to afford the crude product. Chromatography (CH$_2$Cl$_2$/CH$_3$OH 95:5) yielded 1.75 g (81%, 9.5 mmol) of a light brown solid. MS (m/z): 184.3 ([M+H]$^+$).

65.1 2-Chloro-6-(piperidin-4-yloxy)-benzonitrile hydrochloride

2-Chloro-6-(piperidin-4-yloxy)-benzonitrile hydrochloride was prepared in a manner analogous to that described in example 59.2 from 2-chloro-6-fluoro-benzonitrile and 4-hydroxy-piperidine-1-carboxylic acid tert-butyl ester. White solid. MS (m/z): 237.0 ([M+H]$^+$).

65.2 N-trans(4-{2-[4-(3-Chloro-2-cyano-phenoxy)-piperidin-1-yl]-ethyl}-cyclohexyl)-acetamide The title compound was prepared as follows.
N-[trans-4-(2-Oxo-ethyl)-cyclohexyl]-acetamide (intermediate Q, 111 mg, 0.60 mmol) was added to a mixture of 2-chloro-6-(piperidin-4-yloxy)-benzonitrile hydrochloride (131 mg, 0.48 mmol) in 1,2-dichloroethane (5 ml). After stirring for 8 hours at room temperature, sodium triacetoxy-borohydride (Na(AcO)$_3$BH) (152 mg, 0.72 mmol) was added. The reaction mixture was stirred for a further 7 hours before treatment with aq. sat. NaHCO$_3$ sol. Extraction with CH$_2$Cl$_2$, drying over Na$_2$SO$_4$, evaporation of the solvent and chromatography (amino modified silica gel, heptane to ethyl acetate) afforded 114 mg (59%, 0.28 mmol) of product as a white solid. MS (m/z): 404.5 ([M+H]$^+$).

Example 66

N-trans(4-{2-[4-(3-Chloro-4-fluoro-phenoxy)-piperidin-1-yl]-ethyl}-cyclohexyl)-acetamide

66.1 4-(3-Chloro-4-fluoro-phenoxy)-piperidine-1-carboxylic acid tert-butyl ester The title compound was prepared as follows.
Diethyl-azodicarboxylate (DEAD) (214 mg, 1.2 mmol) was added dropwise to a cooled (0° C.) mixture of 4-hydroxy-piperidine-1-carboxylic acid tert-butyl ester (206 mg, 1.0 mmol), 3-chloro-4-fluorophenol (150 mg, 1.0 mmol) and triphenyl phosphine (PPh$_3$) (332 mg, 1.3 mmol) in tetrahydrofuran (THF) (5 ml). The yellow mixture was stirred overnight at room temperature. The solvent was evaporated and the residue purified by chromatography (heptane:ethyl acetate 4:1) to yield 205 mg (61%, 0.62 mmol) of product. Yellowish viscous oil. MS (m/z): 330.3 ([M+H]$^+$).

66.2 N-trans(4-{2-[4-(3-Chloro-4-fluoro-phenoxy)-piperidin-1-yl]-ethyl}-cyclohexyl)-acetamide The title compound was prepared analogously to example 65.2 starting from 4-(3-chloro-4-fluoro-phenoxy)-piperidine-1-carboxylic acid tert-butyl ester. White solid. MS (m/z): 397.1 ([M+H]$^+$).

Example 67

N-trans(4-{2-[4-(2,3,4-Trifluoro-phenoxy)-piperidin-1-yl]-ethyl}-cyclohexyl)-acetamide The title compound was prepared analogously to example 66 starting from 2,3,4-trifluorophenol. White solid. MS (m/z): 399.3 ([M+H]$^+$).

Example 68

Quinoline-4-carboxylic acid (4-{2-[trans 4-(2-chloro-4-fluoro-phenoxy)-3-hydroxy-piperidin-1-yl]-ethyl}-cyclohexyl)-amide Intermediate C 68.1 Trans 4-(2-Chloro-4-fluoro-phenoxy)-3-hydroxy-piperidine-1-carboxylic acid tert-butyl ester The title compound was prepared as follows.
Rac-cis-7-Oxa-3-aza-bicyclo[4.1.0]heptane-3-carboxylic acid tert-butyl ester (1 g, 5 mmol) was solvated in dioxane (5 mL), 2-Chloro-4-Fluorophenol was added (1.471 g, 10 mmol) and sodium hydroxide (0.401 g, 10 mmol). After 20 hours refluxing, the mixture was cooled, ammonium chloride was added and the mixture extracted three times with ethyl acetate. The combined organic phases were dried with magnesium sulfate and concentrated under vacuum. After a flash chromatography with heptane/ethyl acetate 1:1 to 1:2 heptane/ethyl acetate a solid the title compound was obtained as solid (0.778 g, 45% yield). MS (m/e): 404.5 (M+AcO$^-$).

Intermediate D 68.2 Trans 4-(2-Chloro-4-fluoro-phenoxy)-piperidin-3-ol; trifluoroacetic acid salt The title compound was prepared as follows.
0.126 g (0.36 mmol) of trans 4-(2-chloro-4-fluoro-phenoxy)-3-hydroxy-piperidine-1-carboxylic acid tert-butyl ester was solvated in dichloromethane (1.5 mL) and trifluoroacetic acid was added at 0° C. (0.25 mL, 3 mmol). The mixture was stirred at room temperature overnight. NaHCO$_3$ was slowly added until pH 9 and the mixture extracted 3 times with dichloromethane and ethyl acetate. The solvent was evaporated to yield 0.093 g (0.26 mmol, 71%) of a white solid that was used without purification on the next steps. MS (m/e): 246.2 (M+H$^+$).

Intermediate J 68.3 Trans(4-{2-[(4-(2-Chloro-4-fluoro-phenoxy)-3-hydroxy-piperidin-1-yl]-ethyl}-cyclohexyl)-carbamic acid tert-butyl ester According to the synthesis of example 1, the title compound was prepared from Trans 4-(2-Chloro-4-fluoro-phenoxy)-piperidin-3-ol; trifluoroacetic acid salt, Trans-[4-(2-Oxo-ethyl)-cyclohexyl]-carbamic acid tert-butyl ester and sodium triacetoxyborohydride. (MS (m/e): 471.4 (M+H$^+$).

Intermediate K 68.4 Trans 4-{2-[4-(2-chloro-4-fluoro-phenoxy)-3-hydroxy-piperidin-1-yl]-ethyl}-cyclohexyl)-amine According to the synthesis of intermediate K, example 1, the title compound was prepared from Trans(4-{2-[(4-(2-Chloro-4-fluoro-phenoxy)-3-hydroxy-piperidin-1-yl]-ethyl}-cyclohexyl)-carbamic acid tert-butyl ester in dichloromethane and trifluoroacetic acid. MS (m/e): 371.3 (M+H$^+$)

68.5 Quinoline-4-carboxylic acid (4-{2-[trans 4-(2-chloro-4-fluoro-phenoxy)-3-hydroxy-piperidin-1-yl]-ethyl}-cyclohexyl)-amide The title compound was prepared analogously to example 1 from Trans 4-{2-[4-(2-chloro-4-fluoro-phenoxy)-3-hydroxy-piperidin-1-yl]-ethyl}-cyclohexyl)-amine and quinoline-4-carboxylic acid with 2-(1H-benzotriazol-1-yl)-1,1,3,3-tetramethyl uronium tetrafluoroborate (0.035 g, 0.106 mmol) and N-ethyldiisopropylamine in DMF. MS (m/e): 527.3 (M+H$^+$).

Example 69

Quinoline-4-carboxylic acid trans(4-{2-[(3R,4R)-4-(2-chloro-4-fluoro-phenoxy)-3-hydroxy-piperidin-1-yl]-ethyl}-cyclohexyl)-amide 69.1 (3R,4R)-4-(2-Chloro-4-fluoro-phenoxy)-3-hydroxy-piperidine-1-carboxylic acid tert-butyl ester The title compound was prepared as follows.
0.700 g of Trans 4-(2-Chloro-4-fluoro-phenoxy)-3-hydroxy-piperidine-1-carboxylic acid tert-butyl ester (example 68.1) was separated in Chiralpak AD using 10% ethanol/heptane to obtain 0.323 g of (3R,4R)-4-(2-Chloro-4-fluoro-phenoxy)-3-hydroxy-piperidine-1-carboxylic acid tert-butyl ester. MS 405.4 (M+AcO−).

Quinoline-4-carboxylic acid trans(4-{2-[(3R,4R)-4-(2-chloro-4-fluoro-phenoxy)-3-hydroxy-piperidin-1-yl]-ethyl}-cyclohexyl)-amide The title compound was prepared analogously to example 69 from (3R,4R)-4-(2-Chloro-4-fluoro-phenoxy)-3-hydroxy-piperidin-1-yl]-ethyl}-cyclohexyl)-amine and Quinoline-4-carboxylic acid with 2-(1H-benzotriazol-1-yl)-1,1,3,3-tetramethyl uronium tetrafluoroborate (0.035 g, 0.106 mmol) and N-ethyldiisopropylamine in DMF. MS (m/e): 526.3 (M+H$^+$).

Example 70

Quinoline-4-carboxylic acid trans(4-{2-[(3S,4S)-4-(2-chloro-4-fluoro-phenoxy)-3-hydroxy-piperidin-1-yl]-ethyl}-cyclohexyl)-amide 70.1 (3S,4S)-4-(2-Chloro-4-fluoro-phenoxy)-3-hydroxy-piperidine-1-carboxylic acid tert-butyl ester The title compound was prepared as follows.

0.700 g of Trans 4-(2-Chloro-4-fluoro-phenoxy)-3-hydroxy-piperidine-1-carboxylic acid tert-butyl ester (example 69.1) was separated in Chiralpak AD using 10% ethanol/heptane to obtain 0.322 g of (3S,4S)-4-(2-Chloro-4-fluoro-phenoxy)-3-hydroxy-piperidine-1-carboxylic acid tert-butyl ester. MS 405.4 (M+AcO−).

Quinoline-4-carboxylic acid trans(4-{2-[(3S,4S)-4-(2-chloro-4-fluoro-phenoxy)-3-hydroxy-piperidin-1-yl]-ethyl}-cyclohexyl)-amide The title compound was prepared analogously to example 69 from (3S,4S)-4-(2-Chloro-4-fluoro-phenoxy)-3-hydroxy-piperidin-1-yl]-ethyl}-cyclohexyl)-amine and quinoline-4-carboxylic acid with 2-(1H-benzotriazol-1-yl)-1,1,3,3-tetramethyl uronium tetrafluoroborate (0.035 g, 0.106 mmol) and N-ethyldiisopropylamine in dimethylformamide (DMF). MS (m/e): 526.3 (M+H$^+$)

Example 71

Quinoline-4-carboxylic acid trans(4-{2-[4-(4-fluoro-phenoxy)-piperidin-1-yl]-ethyl}-cyclohexyl)-amide Intermediate G Trans-(4-Amino-cyclohexyl)-acetic acid ethyl ester The Title Compound was Prepared as Follows.

Step 1

(4-Nitro-phenyl)-acetic acid (0.005 g, 276 mmol) was added to a stirred solution of 22.08 g of 50% sodium hydroxide solution in 450 mL deionizated water. The clear yellow solution was transferred into a high-pressure autoclave that it charged with 30 g (511 mmol) of water-wet sponge nickel catalyst. The autoclave was sealed, flushed with nitrogen and then pressurized to 115 bar with hydrogen. The reaction mixture was stirred and heated to 125° C. for 48 hours. At that time the autoclave was cooled, vented and charged under nitrogen with another 30 g (511 mmol) of the sponge nickel catalyst. The autoclave was flushed again with nitrogen and then pressurized to 115 bar and the vessel was heated to 130° C. while stirring (a maximum pressure of 130 bars was observed). Hydrogenation was continued for 5 days to 130° C. The autoclave was then cooled, vented and flushed with nitrogen and the contents are removed and filtered through filter aid to remove catalyst. After removal of the solvent, a crude was obtained. The intermediate was used directly in the next step without purification. MS (m/e): 158.3 (M+H$^+$)

Step 2

A solution of the Trans-(4-amino-cyclohexyl)-acetic acid obtained (74 g, 476 mmol) was adjusted to pH 5 with 25% HCl. The mixture was evaporated to dryness and dried under vacuum overnight. The residue was suspended in 146 mL of a 6.5N ethanolic HCl solution and 0.6 L of ethanol was added to the mixture. After 4 hours refluxing, the mixture was cooled, filtered and the filtrate was concentrated to dryness under vacuum. The residue was dissolved in ethanol, treated with ether and cooled overnight in the refrigerator to give the trans-(4-Amino-cyclohexyl)-acetic acid ethyl ester hydrochloride (19.7 g, 32% on the two steps) as a white solid which was filtered and dried under vacuum. MS (m/e): 186.1 (M+H$^+$)

Intermediate L

Trans-{4-[(Quinoline-4-carbonyl)-amino]-cyclohexyl}-acetic acid

The Title Compound was Prepared as Follows.

Step 1

{Trans-4-[(Quinoline-4-carbonyl)-amino]-cyclohexyl}-acetic acid ethyl ester hydrochloride salt A mixture of Trans-(4-Amino-cyclohexyl)-acetic acid ethyl ester hydrochloride (3.63 g, 17 mmol) was solved in dichloromethane (115 mL) and quinoline-4-carbonyl chloride hydrochloride was added (4.184 g, 18 mmol) followed by the slow addition of triethylamine (11.3 mL, 81 mmol) at 0° C. The mixture was stirred at room temperature overnight and the salts obtained are removed by filtration and the filtrate was extracted. The organic layer was washed with NaHCO$_3$ and brine. The organic phases are dried and concentrated to obtain 3.8 g of a crude. After a flash chromatography with heptane/ethyl acetate 4:1 a solid was obtained that was recrystallized with ethyl acetate and n-heptane to obtain the title compound as a pink solid (2.72 g, 42% yield). MS (m/e): 341.3 (M+H$^+$).

Step 2

Trans-{4-[(Quinoline-4-carbonyl)-amino]-cyclohexyl}-acetic acid

4-[(Quinoline-4-carbonyl)-amino]-cyclohexyl}-acetic acid ethyl ester hydrochloride salt (2.7 g, 8 mmol) was reacted with lithium hydroxide monohydrate (3.33 g, 79 mmol) in a mixture of water (65 mL) and tetrahydrofuran (THF) (130 mL) and the mixture was heated at reflux for 5 hours. A ⅔ of the mixture was evaporated and HCl 37% was added until pH 7. The mixture was then evaporated to dryness and 30 mL of water was added and the suspension was filtered to obtain a solid that was recrystallized on toluene (2.2 g, 88.6% yield). MS (m/e): 313.1 (M+H$^+$).

Intermediate M

Trans-{4-[(Quinoline-4-carbonyl)-amino]-cyclohexyl}-thioacetic acid S— ethyl ester 2.19 g of Trans-{4-[(Quinoline-4-carbonyl)-amino]-cyclohexyl}-acetic acid (7 mmol) was added in 1300 mL of dichloromethane. Then 1.8 mL of oxalyl chloride was added (21 mmol). The suspension was heated to reflux for 3 hours and then the cloudy mixture was concentrated under vacuum. The residue was taken up in 500 mL of dichloromethane as a suspension and (1.28 g, 21 mmol) sodium ethylthiolate freshly prepared from 1.45 mL of ethanothiol and 12.07 mL of butyl lithium (1.6 M in toluene) at 0° C. and by stirring in dimethoxyethane (20 mL) for 1 hour at room temperature. The reaction mixture was stirred overnight. NaHCO$_3$ was added and the organic phase was extracted three times with dichloromethane. The organic phases were dried and concentrated and the residue was chromatographed with heptane/ ethyl acetate 1:1 to yield the title compound as a solid (1.97 g, 78.9% yield). MS (m/e): 357.3 (M+H$^+$).

Intermediate N

Quinoline-4-carboxylic acid trans-[4-(2-oxo-ethyl)-cyclohexyl]-amide

The title compound was prepared as follows.

Trans-{4-[(Quinoline-4-carbonyl)-amino]-cyclohexyl}-thioacetic acid S—ethyl ester (1.87 g, 5 mmol) was solved in acetone/methylene chloride (40/40 mL), 0.8 g of molecular sieves were added to the mixture and the solution was stirred for 0.5 h. Then 0.558 g (1 mmol) of palladium on active charcoal 10% was added followed by 1.25 mL (8 mmol) of triethyl-silane. The reaction was stirred for 1.5 hours at room temperature and additional 0.558 g (1 mmol) of palladium on active charcoal 10% and 1.25 mL (8 mmol) of triethyl-silane were added and the stirring was continued for another hour. The mixture was filtrated through celite and the mother liquid was concentrated to obtain after chromatography using heptane/acetate 1:1 1.1 (37.1 mmol, 70.8% yield) of the final compound. MS (m/e): 297.3 (M+H$^+$)

Quinoline-4-carboxylic acid trans(4-{2-[4-(4-fluoro-phenoxy)-piperidin-1-yl]-ethyl}-cyclohexyl)-amide The title compound was prepared as follows.

4-(4-Fluoro-phenoxy)-piperidine (intermediate D, example 1) (0.015 g, 0.076 mmol) was solvated in 1,2-dichloromethane (0.300 mL) and quinoline-4-carboxylic acid trans-[4-(2-oxo-ethyl)-cyclohexyl]-amide (0.025 g, 0.084 mmol) was added. Methanol (0.100 mL) was added to improve solubility and the mixture was stirred overnight. Sodium triacetoxyborohydride (0.029, 0.137 mmol) was added to the clear solution that was stirred 10 hours at room temperature. The mixture was concentrated to dryness and the residue was taken up on methanol and purified with preparative HPLC on reversed phase eluting with acetonitrile/water. The combined product fractions were evaporated under reduced pressure to yield 0.034 g of a white solid (0.07 mmol, 93%). MS (m/e): 476.2 (M+H$^+$)

Example 72

Quinoline-4-carboxylic acid trans(4-{2-[4-(2,3-dichloro-phenoxy)-piperidin-1-yl]-ethyl}-cyclohexyl)-amide The title compound was prepared analogously to example 71 using quinoline-4-carboxylic acid trans-[4-(2-oxo-ethyl)-cyclohexyl]-amide and 4-(2,3-dichloro-phenoxy)-piperidine as starting materials.

Example 73

Quinoline-4-carboxylic acid trans(4-{2-[4-(3,4-dichloro-phenoxy)-piperidin-1-yl]-ethyl}-cyclohexyl)-amide The title compound was prepared analogously to example 71 using quinoline-4-carboxylic acid trans-[4-(2-oxo-ethyl)-cyclohexyl]-amide and 4-(3,4-dichloro-phenoxy)-piperidine as starting materials.

| Ex. No | Systematic name | MW | Starting materials | MW found (M + H)+ |
|---|---|---|---|---|
| 71 | Quinoline-4-carboxylic acid trans (4-{2-[4-(4-fluoro-phenoxy)-piperidin-1-yl]-ethyl}-cyclohexyl)-amide | 475.6 | Quinoline-4-carboxylic acid trans-[4-(2-oxo-ethyl)-cyclohexyl]-amide and 4-(4-Fluoro-phenoxy)-piperidine | 476.2 |
| 72 | Quinoline-4-carboxylic acid trans (4-{2-[4-(2,3-dichloro-phenoxy)-piperidin-1-yl]-ethyl}-cyclohexyl)-amide | 526.5 | Quinoline-4-carboxylic acid trans-[4-(2-oxo-ethyl)-cyclohexyl]-amide and 4-(2,3-dichloro-phenoxy)-piperidine | 526.5 |
| 73 | Quinoline-4-carboxylic acid trans (4-{2-[4-(3,4-dichloro-phenoxy)-piperidin-1-yl]-ethyl}-cyclohexyl)-amide | 505.06 | Quinoline-4-carboxylic acid trans-[4-(2-oxo-ethyl)-cyclohexyl]-amide and 4-(3,4-dichloro-phenoxy)-piperidine | 505.3 |

Example 74

Quinoline-4-carboxylic acid (trans-4-{2-[4-(Pyridin-4-yloxy)-piperidin-1-yl]-ethyl}-cyclohexyl)-amide The title compound was prepared analogously to example 59 starting from 4-(piperidin-4-yloxy)-pyridine (CAS#224178-65-8) and performing the amide coupling reaction with quinoline-4-carboxylic acid. Orange crystals. MS (m/z): 459.3 ([M+H]$^+$).

Example 75

N-(trans-4-{2-[4-(Pyridin-3-yloxy)-piperidin-1-yl]-ethyl}-cyclohexyl)-acetamide

The title compound was prepared analogously to example 59 starting from 3-(piperidin-4-yloxy)-pyridine (CAS#310881-48-2) and performing the amide coupling reaction with acetic acid. Off-white solid. MS (m/z): 346.2 ([M+H]$^+$).

Example 76

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |

-continued

| Ingredients | Per tablet | |
|---|---|---|
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 77

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 78

Injection solutions can have the following composition:

| Compound of formula (I) | 3.0 mg |
|---|---|
| Gelatine | 150.0 mg |
| Phenol | 4.7 mg |
| Sodium carbonate | to obtain a final pH of 7 |
| Water for injection solutions | ad 1.0 ml |

Example 79

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |

-continued

| Partially hydrogenated plant oils | 34.0 mg |
|---|---|
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 80

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 81

The ability of compounds of the present invention to bind to the 5-$HT_{2A}$, $D_3$ and $D_2$ receptors was determined using radioligand binding to cloned receptors selectively expressed in HEK-293 EBNA cells.

Membrane Preparation for Human $D_2$, Human $D_3$ and Human 5-$HT_{2A}$ Receptors HEK-293 EBNA cells were transiently transfected with expression plasmids encoding for the human $D_2$ or $D_3$ dopamine- or for the human 5-$HT_{2A}$ serotonin receptor, respectively. The cells were harvested 48 hours post-transfection, washed three times with cold phosphate buffered saline (PBS) and stored at −80° C. prior to use. The pellet was suspended in cold 50 mM Tris-HCl buffer containing 10 mM EDTA (pH 7.4) and homogenized with a Polytron (Kinematica AG, Basel, Switzerland) for 20-30 seconds at 12.000 rpm. After centrifugation at 48.000×g for 30 minutes at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay Conditions

Aliquots of membrane preparations were thawed at room temperature, resuspended in assay buffer ($D_2$, $D_3$: 50 mM Tris-HCl, 120 mM NaCl, 5 mM $MgCl_2$, 1 mM EDTA, 5 mM KCl, 1.5 mM $CaCl_2$, pH=7.4; $5\text{-}HT_{2A}$: 50 mM Tris-HCl, 10 mM $MgCl_2$, 1 mM EGTA, pH=7.4), homogenized with a Polytron for 20-30 seconds at 12.000 rpm and adjusted to a final concentration of approximately 7.5 μg protein/well ($D_2$, $D_3$) and 15 μg protein/well ($5\text{-}HT_{2A}$), respectively.

The binding affinity (Ki) of the compounds was determined using radioligand binding. Membranes were incubated in a total volume of 200 μl with a fixed concentration of radioligand (final concentration approximately 0.7 nM [$^3$H]-spiperone for $D_2$, 0.5 nM [$^3$H]-spiperone for $D_3$, and 1.1 nM [$^3$H]-ketanserin for $5\text{-}HT_{2A}$) and ten concentrations of test compound ranging between 10 μM-0.1 nM for 1 h at RT. At the end of the incubation, the reaction mixtures were filtered on to unifilter 96-well white microplates with bonded GF/C filters (Packard BioScience, Zudrich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 μM unlabelled spiperone. Per well 45 μl of Microscint 40 (Perkin Elmer, Schwerzenbach, Switzerland) was added, plates for sealed, shaken for 20 min and counted for 3 minutes on a Topcount Microplate Scintillation Counter (Can berra Packard SA, Zu-rich, Switzerland) with quenching correction.

Data Calculation

The CPM value for each duplicate of a concentration of competing compound was averaged (y1), then the % specific binding was calculated according to the equation (((y1−nonspecific)/(total binding−nonspecific))×100). Graphs were plotted with the % specific binding using XLfit, a curve fitting program that iteratively plots the data using Levenburg Marquardt algorithm. The single site competition analysis equation used was y=A+((B−A)/(1+((x/C)$^D$))), where y is the % specific binding, A is the minimum y, B is the maximum y, C is the $IC_{50}$, x is the $\log_{10}$ of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (Ki) was calculated using the Cheng-Prusoff equation Ki=($IC_{50}$/1+([L]/Kd), where [L] is the concentration of radioligand and Kd is the dissociation constant of the radioligand at the receptor as determined by the saturation isotherm.

The compounds of the present invention are selective dual modulators of the serotonin $5\text{-}HT_{2a}$ and dopamine $D_3$ receptors as this is shown with the activity table hereinafter which gives the Ki values in nM for the serotonin $5\text{-}HT_{2a}$, dopamine $D_3$ and dopamine $D_2$ receptors for some examples of the compounds of the present invention:

ACTIVITY TABLE

| | Example | | | |
|---|---|---|---|---|
| | 3 | 11 | 18 | 51 |
| Ki(nM) $D_3/5HT_{2A}/D_2$ | 48/22/1474 | 17/2/321 | 5/2/604 | 29/36/638 |

ACTIVITY TABLE-continued

| | Example | | | |
|---|---|---|---|---|
| | 8 | 13 | 19 | 62 |
| Ki(nM) $D_3/5HT_{2A}/D_2$ | 50/31/843 | 14/3/790 | 12/3/683 | 100/43/3323 |

| | Example | | | |
|---|---|---|---|---|
| | 9 | 15 | 21 | 72 |
| Ki(nM) $D_3/5HT_{2A}/D_2$ | 14/13/574 | 17/2/556 | 3/2/697 | 5/9/319 |

| | Example | | | |
|---|---|---|---|---|
| | 10 | 16 | 24 | 74 |
| Ki(nM) $D_3/5HT_{2A}/D_2$ | 16/22/592 | 11/5/553 | 8/3/453 | 208/60/3004 |

The invention claimed is:
1. A compound according to general formula I:

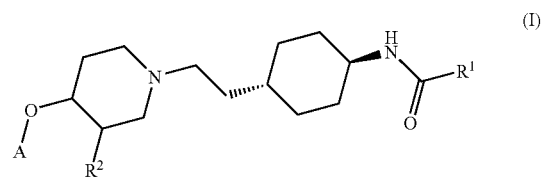

wherein:
A is optionally substituted by at least one substituent, each said substituent independently selected from the group consisting of:
halogen,
cyano,
$C_{1-6}$-alkyl optionally substituted by cyano or $C_{1-6}$-alkoxy,
$C_{1-6}$-alkoxy, and
—S(O)$_2$—$C_{1-6}$-alkyl;
$R^1$ is selected from the group consisting of:
$C_{1-6}$-alkyl optionally substituted by at least one substituent, each of said substituent being independently selected from the group consisting of: halogen, $C_{1-6}$-alkoxy, and aryl optionally substituted by halogen;
$C_{3-10}$-cycloalkyl optionally substituted by one or more $R^a$;
5- to 12-membered heterocycloalkyl optionally substituted by one or more $R^a$;
aryl optionally substituted by one or more $R^a$;
5- to 12-membered heteroaryl optionally substituted by one or more $R^a$; and
—NR$^b$R$^c$, wherein R$^b$ is hydrogen or $C_{1-6}$-alkyl and R$^c$ is hydrogen,
$C_{1-6}$-alkyl or aryl optionally substituted by one or more $R^a$;
each $R^a$ is independently selected from the group consisting of:
halogen;
—S(O)$_2$—$C_{1-6}$-alkyl;
cyano;
oxo;
$C_{1-6}$-alkyl optionally substituted by aryl which is substituted by halogen;

$C_{1-6}$-haloalkyl;
$C_{1-6}$-haloalkoxy;
$C_{1-6}$-alkoxy optionally substituted by 5- to 6-membered heteroaryl which is optionally substituted by $C_{1-6}$-alkyl;
—NH(CO)—$C_{1-6}$-alkyl;
5- to 6-membered heterocycloalkyl; and
5- to 6-membered heteroaryl optionally substituted by $C_{1-6}$-alkyl or oxo; and
$R^2$ is selected from the group consisting of hydrogen and hydroxyl;
or a pharmaceutically-acceptable salt thereof.

2. A compound according to claim 1, wherein A is aryl optionally substituted by at least one substituent, said substituent independently selected from the group consisting of: halogen, cyano and $C_{1-6}$-alkyl substituted by cyano.

3. A compound according to claim 1, wherein $R^1$ is $C_{1-6}$-alkyl optionally substituted by at least one substituent, each of said substituent being independently selected from the group consisting of: halogen and $C_{1-6}$-alkoxy.

4. A compound according to claim 3, said compound being selected from the group consisting of:
N-trans(4-{2-[4-(4-Fluoro-phenoxy)-piperidin-1-yl]-ethyl}-cyclohexyl)-3-methoxy-propionamide;
N-trans(4-{2-[4-(4-Fluoro-phenoxy)-piperidin-1-yl]-ethyl}-cyclohexyl)-acetamide;
N-(4-{2-[4-(2-Chloro-4-fluoro-phenoxy)-piperidin-1-yl]-ethyl}-cyclohexyl)-3-methoxy-propionamide;
N-trans(4-{2-[4-(2-Chloro-4-fluoro-phenoxy)-piperidin-1-yl]-ethyl}-cyclohexyl)-propionamide;
N-trans(4-{2-[4-(2-Chloro-4-fluoro-phenoxy)-piperidin-1-yl]-ethyl}-cyclohexyl)-acetamide;
N-trans(4-{2-[4-(2,4-Difluoro-phenoxy)-piperidin-1-yl]-ethyl}-cyclohexyl)-acetamide;
N-Trans(4-{2-[4-(2-Cyano-4-fluoro-phenoxy)-piperidin-1-yl]-ethyl}-cyclohexyl)-3-methoxy-propionamide;
N-trans(4-{2-[4-(2-Cyano-4-fluoro-phenoxy)-piperidin-1-yl]-ethyl}-cyclohexyl)-acetamide;
N-trans(4-{2-[4-(2-Cyano-4-fluoro-phenoxy)-piperidin-1-yl]-ethyl}-cyclohexyl)-2,2,2-trifluoro-acetamide;
Trans N-(4-{2-[4-(2,3-Dichloro-phenoxy)-piperidin-1-yl]-ethyl}-cyclohexyl)-3-methoxy-propionamide;
N-Trans(4-{2-[4-(2,3-Dichloro-phenoxy)-piperidin-1-yl]-ethyl}-cyclohexyl)-acetamide;
N-trans(4-{2-[4-(2,6-Dichloro-4-fluoro-phenoxy)-piperidin-1-yl]-ethyl}-cyclohexyl)-3-methoxy-propionamide;
N-Trans(4-{2-[4-(2,6-Dichloro-4-fluoro-phenoxy)-piperidin-1-yl]-ethyl}-cyclohexyl)-acetamide;
N-trans(4-{2-[4-(2,4,5-Trifluoro-phenoxy)-piperidin-1-yl]-ethyl}-cyclohexyl)-acetamide;
N-trans(4-{2-[4-(2-Cyano-phenoxy)-piperidin-1-yl]-ethyl}-cyclohexyl)-acetamide;
N-trans(4-{2-[4-(4-Chloro-2-cyano-phenoxy)-piperidin-1-yl]-ethyl}-cyclohexyl)-acetamide;
N-trans(4-{2-[4-(3-Chloro-2-cyano-phenoxy)-piperidin-1-yl]-ethyl}-cyclohexyl)-acetamide;
N-trans(4-{2-[4-(3-Chloro-4-fluoro-phenoxy)-piperidin-1-yl]-ethyl}-cyclohexyl)-acetamide; and
N-trans(4-{2-[4-(2,3,4-Trifluoro-phenoxy)-piperidin-1-yl]-ethyl}-cyclohexyl)-acetamide;
or a pharmaceutically-acceptable salt thereof.

5. A compound according to claim 1, wherein $R^1$ is $C_{3-10}$-cycloalkyl optionally substituted by at least one $R^a$, wherein each $R^a$ is independently a $C_{1-6}$-alkyl.

6. A compound according to claim 5, said compound being selected from the group consisting of:
Cyclopropanecarboxylic acid trans(4-{2-[4-(4-fluoro-phenoxy)-piperidin-1-yl]-ethyl}-cyclohexyl)-amide;
Cyclopropanecarboxylic acid trans(4-{2-[4-(2-chloro-4-fluoro-phenoxy)-piperidin-1-yl]-ethyl}-cyclohexyl)-amide;
Cyclobutanecarboxylic acid trans(4-{2-[4-(2-cyano-4-fluoro-phenoxy)-piperidin-1-yl]-ethyl}-cyclohexyl)-amide;
Cyclopropanecarboxylic acid trans(4-{2-[4-(2-cyano-4-fluoro-phenoxy)-piperidin-1-yl]-ethyl}-cyclohexyl)-amide;
2-Methyl-cyclopropanecarboxylic acid trans(4-{2-[4-(2-cyano-4-fluoro-phenoxy)-piperidin-1-yl]-ethyl}-cyclohexyl)-amide;
Cyclobutanecarboxylic acid trans(4-{2-[4-(2,3-dichloro-phenoxy)-piperidin-1-yl]-ethyl}-cyclohexyl)-amide;
Cyclobutanecarboxylic acid trans(4-{2-[4-(2,6-dichloro-4-fluoro-phenoxy)-piperidin-1-yl]-ethyl}-cyclohexyl)-amide;
Cyclobutanecarboxylic acid trans(4-{2-[4-(2,4,6-trifluoro-phenoxy)-piperidin-1-yl]-ethyl}-cyclohexyl)-amide;
Cyclobutanecarboxylic acid trans(4-{2-[4-(2,4,5-trifluoro-phenoxy)-piperidin-1-yl]-ethyl}-cyclohexyl)-amide;
2-Methyl-cyclopropanecarboxylic acid trans(4-{2-[4-(2,4,5-trifluoro-phenoxy)-piperidin-1-yl]-ethyl}-cyclohexyl)-amide; and
Cyclopropanecarboxylic acid trans(4-{2-[4-(4-chloro-2-cyano-phenoxy)-piperidin-1-yl]-ethyl}-cyclohexyl)-amide; and
or a pharmaceutically-acceptable salt thereof.

7. A compound according to claim 1, wherein $R^1$ is 5- to 12-membered heterocycloalkyl.

8. A compound according to claim 7, said compound being selected from the group consisting of:
Tetrahydro-pyran-4-carboxylic acid trans(4-{2-[4-(4-fluoro-phenoxy)-piperidin-1-yl]-ethyl}-cyclohexyl)-amide;
Tetrahydro-pyran-4-carboxylic acid trans(4-{2-[4-(2-chloro-4-fluoro-phenoxy)-piperidin-1-yl]-ethyl}-cyclohexyl)-amide;
Tetrahydro-pyran-4-carboxylic acid trans(4-{2-[4-(2,4-difluoro-phenoxy)-piperidin-1-yl]-ethyl}-cyclohexyl)-amide;
Tetrahydro-pyran-4-carboxylic acid trans(4-{2-[4-(2-cyano-4-fluoro-phenoxy)-piperidin-1-yl]-ethyl}-cyclohexyl)-amide;
Tetrahydro-pyran-4-carboxylic acid trans(4-{2-[4-(2,3-dichloro-phenoxy)-piperidin-1-yl]-ethyl}-cyclohexyl)-amide;
Tetrahydro-furan-2-carboxylic acid trans(4-{2-[4-(2,6-dichloro-4-fluoro-phenoxy)-piperidin-1-yl]-ethyl}-cyclohexyl)-amide;
Tetrahydro-pyran-4-carboxylic acid trans(4-{2-[4-(2,6-dichloro-4-fluoro-phenoxy)-piperidin-1-yl]-ethyl}-cyclohexyl)-amide;
Tetrahydro-furan-2-carboxylic acid trans(4-{2-[4-(2,4,6-trifluoro-phenoxy)-piperidin-1-yl]-ethyl}-cyclohexyl)-amide;
Tetrahydro-pyran-4-carboxylic acid trans(4-{2-[4-(2,4,5-trifluoro-phenoxy)-piperidin-1-yl]-ethyl}-cyclohexyl)-amide; and Tetrahydro-pyran-4-carboxylic acid trans(4-{2-[4-(4-chloro-2-cyano-phenoxy)-piperidin-1-yl]-ethyl}-cyclohexyl)-amide;

or a pharmaceutically-acceptable salt thereof.

9. A compound according to claim 1, wherein $R^1$ is aryl optionally substituted by at least one $R^a$, wherein each $R^a$ is independently selected from the group consisting of: halogen, $C_{1-6}$-alkoxy, —$S(O)_2$—$C_{1-6}$-alkyl, and 5- to 6-membered heteroaryl optionally substituted by $C_{1-6}$-alkyl.

10. A compound according to claim 9, said compound being selected from the group consisting of:

4-Chloro-N-trans(4-{2-[4-(4-fluoro-phenoxy)-piperidin-1-yl]-ethyl}-cyclohexyl)-benzamide;

N-trans(4-{2-[4-(4-Fluoro-phenoxy)-piperidin-1-yl]-ethyl}-cyclohexyl)-3-(5-methyl-[1,2,4]oxadiazol-3-yl)-benzamide;

N-trans(4-{2-[4-(4-Fluoro-phenoxy)-piperidin-1-yl]-ethyl}-cyclohexyl)-4-methanesulfonyl-benzamide;

N-trans(4-{2-[4-(2-Chloro-4-fluoro-phenoxy)-piperidin-1-yl]-ethyl}-cyclohexyl)-4-methanesulfonyl-benzamide;

4-Chloro-N-trans(4-{2-[4-(2-chloro-4-fluoro-phenoxy)-piperidin-1-yl]-ethyl}-cyclohexyl)-benzamide;

N-trans(4-{2-[4-(2-Chloro-4-fluoro-phenoxy)-piperidin-1-yl]-ethyl}-cyclohexyl)-3-(5-methyl-[1,2,4]oxadiazol-3-yl)-benzamide;

4-Chloro-N-trans(4-{2-[4-(2-cyano-4-fluoro-phenoxy)-piperidin-1-yl]-ethyl}-cyclohexyl)-benzamide;

N-trans(4-{2-[4-(2-Cyano-4-fluoro-phenoxy)-piperidin-1-yl]-ethyl}-cyclohexyl)-4-methoxy-benzamide;

4-Methoxy-N-trans(4-{2-[4-(2,4,6-trifluoro-phenoxy)-piperidin-1-yl]-ethyl}-cyclohexyl)-benzamide;

4-Chloro-N-trans(4-{2-[4-(2,4,6-trifluoro-phenoxy)-piperidin-1-yl]-ethyl}-cyclohexyl)-benzamide;

4-Methoxy-N-trans(4-{2-[4-(2,4,5-trifluoro-phenoxy)-piperidin-1-yl]-ethyl}-cyclohexyl)-benzamide;

4-Chloro-N-trans(4-{2-[4-(2,4,5-trifluoro-phenoxy)-piperidin-1-yl]-ethyl}-cyclohexyl)-benzamide; and N-trans(4-{2-[4-(2-Cyano-phenoxy)-piperidin-1-yl]-ethyl}-cyclohexyl)-4-ethoxy-benzamide;

or a pharmaceutically-acceptable salt thereof.

11. A compound according to claim 1, wherein $R^1$ is 5- to 12-membered heteroaryl.

12. A compound according to claim 11, said compound being selected from the group consisting of:

1H-Indole-2-carboxylic acid trans(4-{2-[4-(4-fluoro-phenoxy)-piperidin-1-yl]-ethyl}-cyclohexyl)-amide;

Quinoline-4-carboxylic acid trans(4-{2[4-(2-chloro-4-fluoro-phenoxy)-piperidin-1-yl]-ethyl}-cyclohexyl)-amide;

Quinoline-6-carboxylic acid trans(4-{2-[4-(2,4-difluoro-phenoxy)-piperidin-1-yl]-ethyl}-cyclohexyl)-amide;

Quinoline-4-carboxylic acid trans(4-{2-[4-(2,4-difluoro-phenoxy)-piperidin-1-yl]-ethyl}-cyclohexyl)-amide;

Thiophene-2-carboxylic acid trans(4-{2-[4-(2-cyano-4-fluoro-phenoxy)-piperidin-1-yl]-ethyl}-cyclohexyl)-amide;

Thiophene-2-carboxylic acid trans(4-{2-[4-(2,3-dichloro-phenoxy)-piperidin-1-yl]-ethyl}-cyclohexyl)-amide;

Thiophene-2-carboxylic acid trans(4-{2-[4-(2,6-dichloro-4-fluoro-phenoxy)-piperidin-1-yl]-ethyl}-cyclohexyl)-amide;

Thiophene-2-carboxylic acid trans(4-{2-[4-(2,4,5-trifluoro-phenoxy)-piperidin-1-yl]-ethyl}-cyclohexyl)-amide;

Thiophene-2-carboxylic acid trans(4-{2-[4-(4-cyano-2-fluoro-phenoxy)-piperidin-1-yl]-ethyl}-cyclohexyl)-amide;

Quinoline-4-carboxylic acid trans(4-{2-[4-(2-cyano-phenoxy)-piperidin-1-yl]-ethyl}-cyclohexyl)-amide;

Quinoline-4-carboxylic acid (4-{2-[trans 4-(2-chloro-4-fluoro-phenoxy)-3-hydroxy-piperidin-1-yl]-ethyl}-cyclohexyl)-amide;

Quinoline-4-carboxylic acid trans(4-{2-[(3R,4R)-4-(2-chloro-4-fluoro-phenoxy)-3-hydroxy-piperidin-1-yl]-ethyl}-cyclohexyl)-amide;

Quinoline-4-carboxylic acid trans(4-{2-[(3S,4S)-4-(2-chloro-4-fluoro-phenoxy)-3-hydroxy-piperidin-1-yl]-ethyl}-cyclohexyl)-amide;

Quinoline-4-carboxylic acid trans(4-{2-[4-(4-fluoro-phenoxy)-piperidin-1-yl]-ethyl}-cyclohexyl)-amide;

Quinoline-4-carboxylic acid trans(4-{2-[4-(2,3-dichloro-phenoxy)-piperidin-1-yl]-ethyl}-cyclohexyl)-amide; and Quinoline-4-carboxylic acid trans(4-{2-[4-(3,4-dichloro-phenoxy)-piperidin-1-yl]-ethyl}-cyclohexyl)-amide;

or a pharmaceutically-acceptable salt thereof.

13. A compound according to claim 1, wherein $R^1$ is —$NR^bR^c$, $R^b$ is hydrogen, and $R^c$ is hydrogen or aryl optionally substituted by at least one $R^a$, wherein each $R^a$ is independently selected from the group consisting of: halogen and $C_{1-6}$-alkyl.

14. A compound according to claim 13, said compound being selected from the group consisting of:

1-(4-Chloro-phenyl)-3-trans(4-{2-[4-(4-fluoro-phenoxy)-piperidin-1-yl]-ethyl}-cyclohexyl)-urea;

1-trans(4-{2-[4-(4-Fluoro-phenoxy)-piperidin-1-yl]-ethyl}-cyclohexyl)-3-p-tolyl-urea;

1-trans(4-{2-[4-(2-Chloro-4-fluoro-phenoxy)-piperidin-1-yl]-ethyl}-cyclohexyl)-3-p-tolyl-urea; and 1-trans(4-{2-[4-(2-Chloro-4-fluoro-phenoxy)-piperidin-1-yl]-ethyl}-cyclohexyl)-3-(4-chloro-phenyl)-urea;

or a pharmaceutically-acceptable salt thereof of such compounds.

15. A process for the preparation of a compound according to claim 1 wherein:

A is aryl optionally substituted by at least one substituent, each said substituent independently selected from the group consisting of:

halogen, cyano, $C_{1-6}$-alkyl optionally substituted by cyano or $C_{1-6}$-alkoxy, $C_{1-6}$-alkoxy, and —$S(O)_2$—$C_{1-6}$-alkyl;

$R^1$ is selected from the group consisting of:

$C_{1-6}$-alkyl optionally substituted by at least one substituent, each of said substituent being independently selected from the group consisting of: halogen, $C_{1-6}$-alkoxy, and aryl optionally substituted by halogen;

$C_{3-10}$-cycloalkyl optionally substituted by one or more $R^a$;

5- to 12-membered heterocycloalkyl optionally substituted by one or more $R^a$;

aryl optionally substituted by one or more $R^a$; and 5- to 12-membered heteroaryl optionally substituted by one or more $R^a$;

each $R^a$ is independently selected from the group consisting of:
halogen;
—S(O)$_2$—C$_{1-6}$-alkyl;
cyano;
oxo;
C$_{1-6}$-alkyl optionally substituted by aryl which is substituted by halogen;
C$_{1-6}$-haloalkyl;
C$_{1-6}$-haloalkoxy;
C$_{1-6}$-alkoxy optionally substituted by 5- to 6-membered heteroaryl which is optionally substituted by C$_{1-6}$-alkyl;
—NH(CO)—C$_{1-6}$-alkyl;
5- to 6-membered heterocycloalkyl; and
5- to 6-membered heteroaryl optionally substituted by C$_{1-6}$-alkyl or oxo; and
$R^2$ is selected from the group consisting of hydrogen and hydroxyl;
said process comprising the step of
reacting a compound of the formula II,

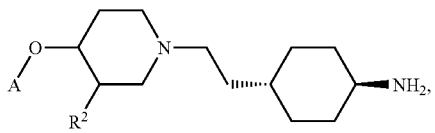

(II)

with an acid of the formula III,

HOOCR$^1$   (III)

in the presence of a coupling reagent.

16. A process for the preparation of a compound according to claim 1 wherein:
A is aryl and optionally substituted by at least one substituent, each said substituent independently selected from the group consisting of:
halogen,
cyano,
C$_{1-6}$-alkyl optionally substituted by cyano or C$_{1-6}$-alkoxy,
C$_{1-6}$-alkoxy, and
—S(O)$_2$—C$_{1-6}$-alkyl;
$R^1$ is —NR$^b$R$^c$, wherein R$^b$ is hydrogen or C$_{1-6}$-alkyl and R$^c$ is aryl optionally substituted by one or more $R^a$;
each $R^a$ is independently selected from the group consisting of:
halogen;
—S(O)$_2$—C$_{1-6}$-alkyl;
cyano;
oxo;
C$_{1-6}$-alkyl optionally substituted by aryl which is substituted by halogen;
C$_{1-6}$-haloalkyl;
C$_{1-6}$-haloalkoxy;
C$_{1-6}$-alkoxy optionally substituted by 5- to 6-membered heteroaryl which is optionally substituted by C$_{1-6}$-alkyl;
—NH(CO)—C$_{1-6}$-alkyl;
5- to 6-membered heterocycloalkyl; and
5- to 6-membered heteroaryl optionally substituted by C$_{1-6}$-alkyl or oxo; and
$R^2$ is selected from the group consisting of hydrogen and hydroxyl;
said process comprising the step of reacting a compound of the formula II,

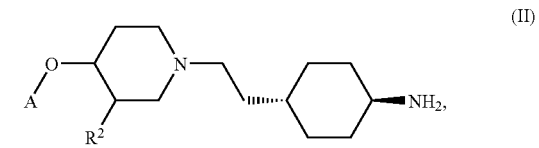

(II)

with an isocyanate or para nitro carbamate.

17. A pharmaceutical composition comprising a compound according to claim 1 and a pharmaceutically acceptable excipient.

\* \* \* \* \*

UNITED STATES PATENT AND TRADEMARK OFFICE
CERTIFICATE OF CORRECTION

| | | |
|---|---|---|
| PATENT NO. | : 7,795,437 B2 | Page 1 of 1 |
| APPLICATION NO. | : 11/876007 | |
| DATED | : September 14, 2010 | |
| INVENTOR(S) | : Gobbi et al. | |

It is certified that error appears in the above-identified patent and that said Letters Patent is hereby corrected as shown below:

Claim 1, Column 54, line 34: "A is optionally substituted by at least one substituent, each" should read -- A is aryl optionally substituted by at least one substituent, each --.

Signed and Sealed this
Twenty-second Day of February, 2011

David J. Kappos
*Director of the United States Patent and Trademark Office*